(12) United States Patent
Akiyama

(10) Patent No.: US 9,200,009 B2
(45) Date of Patent: Dec. 1, 2015

(54) POLYCYCLIC PYRIDONE DERIVATIVE HAVING INTEGRASE INHIBITORY ACTIVITY

(71) Applicant: Shionogi & Co., Ltd., Osaka-shi, Osaka (JP)

(72) Inventor: Toshiyuki Akiyama, Toyonaka (JP)

(73) Assignee: SHIONOGI & CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 14/351,110

(22) PCT Filed: Oct. 12, 2012

(86) PCT No.: PCT/JP2012/076386
§ 371 (c)(1),
(2) Date: Apr. 10, 2014

(87) PCT Pub. No.: WO2013/054862
PCT Pub. Date: Apr. 18, 2013

(65) Prior Publication Data
US 2014/0256937 A1 Sep. 11, 2014

(30) Foreign Application Priority Data
Oct. 12, 2011 (JP) .................................. 2011-224467

(51) Int. Cl.
*C07D 498/14* (2006.01)
*A61K 31/4985* (2006.01)
*A61K 31/437* (2006.01)
*C07D 471/22* (2006.01)

(52) U.S. Cl.
CPC ............ *C07D 498/14* (2013.01); *A61K 31/437* (2013.01); *A61K 31/4985* (2013.01); *C07D 471/22* (2013.01)

(58) Field of Classification Search
CPC .................................................... C07D 498/14
USPC .................................. 544/95, 346; 514/230.2
See application file for complete search history.

(56) References Cited

U.S. PATENT DOCUMENTS

| | | |
|---|---|---|
| 2004/0229909 A1 | 11/2004 | Kiyama et al. |
| 2005/0054645 A1 | 3/2005 | Miyazaki et al. |
| 2009/0143356 A1 | 6/2009 | Yoshida et al. |
| 2012/0108564 A1 | 5/2012 | Miyazaki et al. |
| 2012/0184734 A1 | 7/2012 | Akiyama et al. |
| 2013/0096109 A1 | 4/2013 | Hattori et al. |

FOREIGN PATENT DOCUMENTS

| | | |
|---|---|---|
| EP | 1950212 | 7/2008 |
| EP | 2042502 | 4/2009 |
| EP | 2045242 | 4/2009 |
| EP | 2465580 | 6/2012 |
| JP | H02-096506 | 4/1990 |
| JP | H02-108668 | 4/1990 |
| JP | H02-108683 | 4/1990 |
| JP | 2004-244320 | 9/2004 |
| JP | 2008-540343 | 11/2008 |
| WO | WO 2004/024693 | 3/1994 |
| WO | WO 03/016275 | 2/2003 |
| WO | WO 03/035076 | 5/2003 |
| WO | WO 2004/004657 | 1/2004 |
| WO | WO 2005/016927 | 2/2005 |
| WO | WO 2006/116764 | 11/2006 |
| WO | WO 2007/049675 | 5/2007 |
| WO | WO 2010/068262 | 6/2010 |
| WO | WO 2010/147068 | 12/2010 |
| WO | WO 2011/105590 | 1/2011 |
| WO | WO 2011/129095 | 10/2011 |

*Primary Examiner* — Kahsay Habte
(74) *Attorney, Agent, or Firm* — Ropes & Gray LLP; James F. Haley, Jr.; Yang Xu

(57) ABSTRACT

The present invention relates to a novel compound having an antiviral effect, more specifically, a pyridone derivative having HIV integrase inhibitory activity, and a medicament containing the same, in particular, an anti-HIV agent. The compound of the present invention has integrase inhibitory activity and/or cell proliferation inhibitory activity against viruses, in particular, HIV and drug-resistant strains thereof. Thus, the compound is useful in preventing or treating various diseases, viral infections (for example, AIDS), and the like in which integrase participates.

11 Claims, No Drawings

POLYCYCLIC PYRIDONE DERIVATIVE HAVING INTEGRASE INHIBITORY ACTIVITY

This application is a national stage application under 35 U.S.C. §371 of International Patent Application No. PCT/JP2012/076386, filed on Oct. 12, 2012, which claims the benefit of Japanese Patent Application No. 2011-224467, filed on Oct. 12, 2011. The disclosure of each of these referenced applications is incorporated by reference herein in its entirety.

TECHNICAL FIELD

The present invention relates to novel compounds having antiviral activity, more particularly, polycyclic pyridone derivatives having HIV integrase inhibitory activity; and a medicament containing the same, particularly an anti-HIV agent.

BACKGROUND ART

Among viruses, human immunodeficiency virus (hereafter, referred to as HIV), a kind of retrovirus, is known to cause acquired immunodeficiency syndrome (hereafter, referred to as AIDS). The therapeutic agent for AIDS is mainly selected from a group of reverse transcriptase inhibitors (e.g., AZT, 3TC, etc.) and protease inhibitors (e.g., Indinavir, etc.), but they are proved to be accompanied by the following problems: side effects such as nephropathy, the emergence of resistant viruses, and the like. Thus, the development of anti-HIV agents having the other mechanisms of action therefrom has been desired.

On the other hand, currently, a multiple combination therapy is reported to be efficient in treatment for AIDS because of the frequent emergence of the resistant mutant virus. Two kinds of reverse transcriptase inhibitors and protease inhibitors are clinically used as an anti-HIV agent; however agents having the same mechanism of action often exhibit cross-resistance or only an additional activity. Therefore, development of anti-HIV agents having the other mechanism of action is desired.

Under the circumstances above, an integrase inhibitor has been focused on as an anti-HIV agent having a novel mechanism of action (Ref: Patent Documents 1 and 2). As an anti-HIV agent having such a mechanism of action, known are carbamoyl-substituted hydroxypyrimidinone derivative (Ref: Patent Document 3) and carbamoyl-substituted hydroxypyrrolidione derivative (Ref: Patent Document 4). Further, a patent application concerning carbamoyl-substituted hydroxypyridone derivative has been filed (Ref: Patent Document 5, Example 8).

Further, other known carbamoylpyridone derivatives include 5-alkoxypyridine-3-carboxamide derivatives and γ-pyrone-3-carboxamide derivatives, which are a plant growth inhibitor or herbicide (Ref: Patent Documents 6-8).

Furthermore, other HIV integrase inhibitors include nitrogen-containing condensed cyclic compounds (Ref: Patent Document 9).

Moreover, other HIV integrase inhibitors are known, and in such compounds, the terminal of an amide side chain is aryl (Ref: Patent Documents 10 and 11). In addition, a bicyclic HIV integrase inhibitor is known (Ref: Patent Document 12).

Further, the present applicant filed a patent application of an anti-influenza agent comprising a nitrogen-containing condensed cyclic compound as an active ingredient (Ref: Patent Document 13).

In addition, the present applicant filed a patent application of an HIV integrase inhibitor comprising a nitrogen-containing condensed cyclic compound as an active ingredient (PCT/JP2011/002139).

PRIOR ART REFERENCES

Patent Document

[Patent Document 1] International Publication No. 03/016275 pamphlet
[Patent Document 2] International Publication No. 2004/024693 pamphlet
[Patent Document 3] International Publication No. 03/035076 pamphlet
[Patent Document 4] International Publication No. 2004/004657 pamphlet
[Patent Document 5] Japanese Laid-Open Publication No. 2004-244320
[Patent Document 6] Japanese Laid-Open Publication No. 2-108668
[Patent Document 7] Japanese Laid-Open Publication No. 2-108683
[Patent Document 8] Japanese Laid-Open Publication No. 2-96506
[Patent Document 9] International Publication No. 2005/016927 pamphlet
[Patent Document 10] International Publication No. 2006/116764 pamphlet
[Patent Document 11] International Publication No. 2007/049675 pamphlet
[Patent Document 12] International Publication No. 2011/105590 pamphlet
[Patent Document 13] International Publication No. 2010/147068 pamphlet

SUMMARY OF THE INVENTION

Problems to be Solved by the Invention

Under such the circumstances, the development of a novel integrase inhibitor has been desired.

Means to Solve the Problems

The present inventors intensively studied to find that a novel pyridone derivative has potent HIV integrase inhibitory activity. Moreover, the present inventors have discovered that a compound of the present invention and a medicament containing the same are useful as an antiviral agent (e.g., antiretroviral agent, anti-HIV agent, anti-HTLV-1 (Human T cell leukemia virus type 1) agent, anti-FIV (Feline immunodeficiency virus) agent, anti-SIV (Simian immunodeficiency virus) agent), especially an anti-HIV agent, an anti-AIDS agent, a therapeutic for associated diseases, or the like, to accomplish the present invention shown below.

The formula (I-1):

(1) A compound represented by any formula of the following:

[Chemical formula 1]

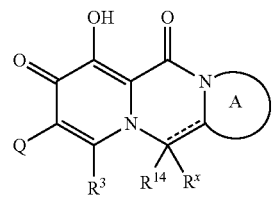

(I-1)

(wherein
Q is a carbocyclic group that is optionally substituted and optionally condensed, or a heterocyclic group that is optionally substituted and optionally condensed;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, an optionally substituted heterocyclic group, an optionally substituted heterocyclyloxy group, or optionally substituted amino;

the A ring is an optionally substituted heterocycle;

$R^{14}$ and $R^X$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, an optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of O, S, SO, $SO_2$, $NR^5$ (wherein $R^5$ is, independent of $R^4$, selected from the same substituent group as $R^4$), —N═, and ═N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, or optionally substituted aminocarbonyl;

the broken line represents the presence or absence of a bond;

with the proviso that when the broken line represents the presence of a bond, $R^X$ is not present);

the formula (I-2):

[Chemical formula 2]

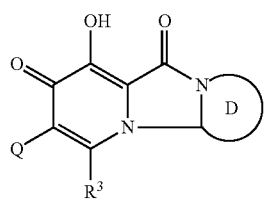

(I-2)

(wherein
the D ring is an optionally substituted heterocycle; and
other symbols are defined the same as above); and the formula (I-3):

[Chemical formula 3]

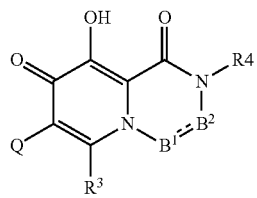

(I-3)

(wherein
the broken line represents the presence or absence of a bond;

either one of $B^1$ and $B^2$ is $CR^{20}R^{21}$ and the other is $NR^{22}$, and in this case, the broken line represents the absence of a bond;

when $B^2$ is $NR^{22}$, $R^4$ and $R^{22}$ may be taken together to form an optionally substituted heterocycle;

when $B^2$ is $CR^{20}R^{21}$, $R^4$ and $R^{21}$ may be taken together to form an optionally substituted heterocycle;

or $B^1$ and $B^2$ are each independently C, $CR^{23}$, or N, and in this case, the broken line represents the presence of a bond, and/or the $B^1$ and $B^2$ parts are taken together to form an optionally substituted heterocycle or an optionally substituted carbocycle;

$R^{20}$, $R^{21}$, $R^{22}$, and $R^{23}$ are each independently, hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, an optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of O, S, SO, $SO_2$, $NR^5$ (wherein $R^5$ is, independent of $R^4$, selected from the same substituent group as $R^4$), —N═, and ═N—) hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, substituted (thio)urea, or substituted sulfonyl; and $R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, an optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, $SO_2$, $NR^a$ (wherein $R^a$ is hydrogen or lower alkyl), —N═, and ═N—); and other symbols are defined the same as above),
or a pharmaceutically acceptable salt thereof.

(2) The compound according to the above-described (1) represented by the following formula:

[Chemical formula 4]

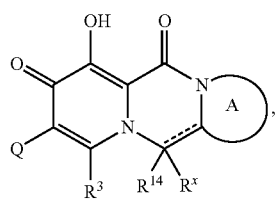
(I-1)

or a pharmaceutically acceptable salt thereof,
wherein each symbol is defined the same as above.

(3) The compound according to the above-described (1) or (2), or a pharmaceutically acceptable salt thereof, wherein (Q) is an optionally substituted heterocyclic group.

(4) The compound according to the above-described (3), or a pharmaceutically acceptable salt thereof, wherein the "heterocyclic group" of Q is a 5-7 membered monocyclic heterocyclic group.

(5) The compound according to the above-described (3), or a pharmaceutically acceptable salt thereof, wherein the heterocyclic group of the "optionally substituted heterocyclic group" of Q is represented by any formula of the following:

[Chemical formula 5]

(1)
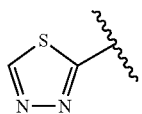

(2)
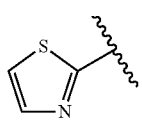

(3)
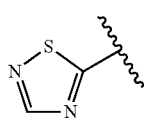

(4)
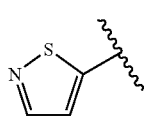

(5)
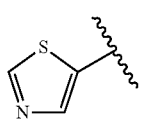

(6)
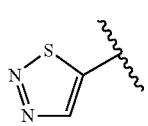

-continued (7)
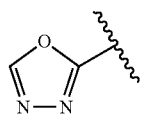

(8)
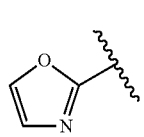

(9)
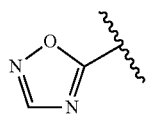

(10)
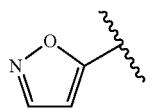

(11)
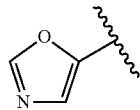

(12)
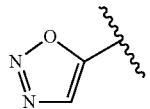

(13)
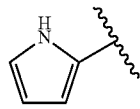

(14)
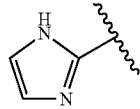

(15)
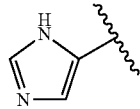

(16)
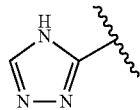

(6) The compound according to any of the above-described (1) to (5), or a pharmaceutically acceptable salt thereof, wherein a substituent(s) in the "optionally substituted" on Q is the same or different, 1 to 4 substituent(s) selected from Substituent group A.
Substituent group A: lower alkyl, lower alkoxy, halogen, halogenated lower alkyl, halogenated lower alkoxy, and the formula:

[Chemical formula 6]

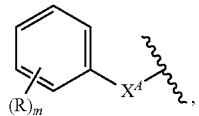

(B)

wherein $X^A$ is a group selected from the following group:
$X^{A1}$: a single bond;
$X^{A2}$: a group selected from C=O and C=S;
$X^{A3}$: a heteroatom group selected from O, S, SO, SO$_2$, and NR$^{1'}$ wherein R$^{1'}$ is hydrogen or lower alkyl;
$X^{A4}$; a group formed by linking the same or different, two or more groups selected from $X^{A2}$ and $X^{A3}$;
$X^{A5}$: a group selected from —N=N—, —C(R$^{1'}$)=N—, or —N=C(R$^{1'}$)— wherein R$^{1'}$ is hydrogen or lower alkyl;
$X^{A6}$: optionally substituted lower alkylene or optionally substituted lower alkenylene;
$X^{A7}$: $X^{A6}$ intervened by one or any two or more groups selected from $X^{A2}$, $X^{A3}$, $X^{A4}$, and $X^{A5}$; and
$X^{A8}$: a spacer consisting of any combination of $X^{A1}$ to $X^{A7}$;
R is a group independently selected from the following group:
(1) lower alkyl,
(2) lower alkoxy,
(3) halogen,
(4) halogenated lower alkyl,
(5) halogenated lower alkoxy, and
(6) lower cycloalkyl; and
m is an integer of 0 to 5.
(7) The compound according to the above-described (1) or (2), or a pharmaceutically acceptable salt thereof, wherein Q is represented by any formula of the following:

[Chemical formula 7]

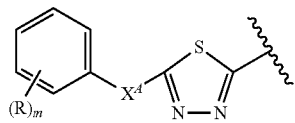

(1)

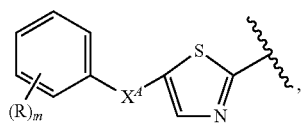

(2)

wherein each symbol is defined the same as the above-described (6).
(8) The compound according to the above-described (7), or a pharmaceutically acceptable salt thereof, wherein $X^A$ is lower alkylene; R is independently lower alkoxy, halogen, or halogenated lower alkyl; m is 1 or 2.
(9) The compound according to the above-described (1), or a pharmaceutically acceptable salt thereof, wherein the compound is represented by any formula of the following:

[Chemical formula 8]

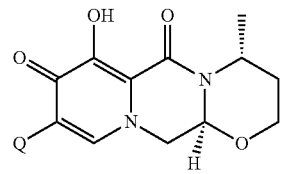

(I-1-1)

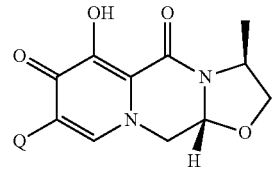

(I-1-2)

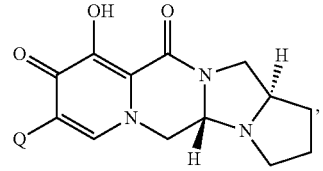

(I-1-3)

wherein Q is defined the same as the above-described (1).
(10) A pharmaceutical composition comprising a compound according to any of the above-described (1) to (9), or a pharmaceutically acceptable salt thereof.
(11) The pharmaceutical composition according to the above-described (10), which has anti-HIV action.
(12) The pharmaceutical composition according to the above-described (10), which has an HIV integrase inhibitory action.

The present invention further provides a method of preventing or treating HIV that is characterized by administering an effective amount of the above-described compound to a human.

The present invention further provides the above-described compound for using as an anti-HIV agent.

Effect of the Invention

The present compound has integrase inhibitory activity and/or cell proliferation inhibitory activity against viruses, in particular, HIV and drug-resistant strains thereof. Thus, the compound is useful in preventing or treating various diseases, viral infections (e.g., AIDS), and the like in which integrase participates. More preferably, the present compound is also excellent in resistance profile that it is difficult for the compound to cause a new HIV-resistant virus, and the like. Further preferably, the present compound is useful as a pharmaceutical agent that is excellent in solubility, peroral absorbability, metabolic stability, bioavailability or the like, and for which there is little concern about cytotoxicity and a side effect (e.g., mutagenicity, the QT interval prolongation of the electrocardiogram).

MODE FOR CARRYING OUT THE INVENTION

The terms used herein are explained below. Each term, alone or in combination with another term, means as follows.
"Lower alkylene" means a linear or branched $C_{1-6}$ lower alkylene such as methylene, ethylene, trimethylene, propylene, tetramethylene, ethylethylene, pentamethylene, hexamethylene, or the like. Preferred is a $C_{1-4}$ linear lower alkylene such as methylene, ethylene, trimethylene, or tetramethylene. More preferred is methylene or ethylene.

"Lower alkenylene" means a linear or branched $C_{2-6}$ lower alkenylene group, which consists of the above "Lower alkylene" having one or more double bonds, such as vinylene, propylene, or butenylene. Preferred is a $C_{2-3}$ linear lower alkenylene such as vinylene or propylene.

"Alkyl" means a linear or branched $C_{1-10}$ alkyl group such as methyl, ethyl, n-propyl, isopropyl, n-butyl, isobutyl, sec-butyl, tert-butyl, n-pentyl, isopentyl, neopentyl, tert-pentyl n-hexyl, isohexyl n-heptyl, n-octyl, n-nonyl, n-decyl, and the like. Preferred is a $C_{1-6}$ lower alkyl and more preferred is a $C_{1-4}$ lower alkyl, such as methyl, ethyl, n-propyl, isopropyl, n-butyl, isobutyl, sec-butyl, text-butyl, n-pentyl, isopentyl, neopentyl, tert-pentyl, n-hexyl, and isohexyl.

When lower alkyl is intervened by —N= or =N—, the lower alkyl may have a double bond to form, for example, —CH$_2$—N=CH$_2$, —CH=N—CH$_2$, or the like.

"Alkenyl" means a linear or branched $C_{2-8}$ alkenyl, which consists of the above "alkyl" having one or more double bonds, such as vinyl, 1-propenyl, 2-propenyl, 1-butenyl, 2-butenyl, 3-butenyl, 1,3-butadienyl, 3-methyl-2-butenyl, and the like. Preferred is $C_{2-6}$ lower alkenyl, and more preferred is $C_{2-4}$ lower alkenyl.

"Lower alkenyloxy" means an oxy attached to the above "lower alkenyl", such as vinyloxy, 1-propenyloxy, 2-propenyloxy, 1-butenyloxy, 2-butenyloxy, 3-butenyloxy, 1,3-butadienyloxy, 3-methyl-2-butenyloxy, and the like.

"Alkynyl" means a linear or branched $C_{2-8}$ alkenyl, which consists of the above "alkyl" having one or more triple bonds, such as ethynyl, propargyl, and the like. Preferred is $C_{2-6}$ lower alkynyl, and more preferred is $C_{2-4}$ lower alkynyl.

"Carbocyclic group" means a saturated or unsaturated $C_{3-10}$ carbocyclic group, and includes cycloalkyl, cycloalkenyl, and aryl.

"Cycloalkyl" means a $C_{3-10}$ cyclic saturated hydrocarbon group, such as cyclopropyl, cyclobutyl, cyclopentyl, cyclohexyl, cyclopentyl, cyclooctyl, and the like. Preferred is $C_{3-6}$ cycloalkyl.

"Cycloalkyl lower alkyl" means a lower alkyl substituted with the above cycloalkyl, such as cyclopropylmethyl, cyclopropylethyl, cyclobutylmethyl, cyclopentylmethyl, cyclohexylmethyl, cyclohexylethyl, and the like. Preferred is $C_{3-6}$ cycloalkyl lower alkyl.

"Aryl" means a monocyclic aromatic hydrocarbon group (phenyl) and a polycyclic aromatic hydrocarbon (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, and the like). Preferred is phenyl or naphthyl (e.g., 1-napthyl, 2-naphthyl).

"Aralkyl" or "aryl lower alkyl" means the above "lower alkyl" substituted with one to three of the above "aryl", such as benzyl, diphenylmethyl, triphenylmethyl, phenethyl, 1-napthylmethyl, 2-napthylmethyl, and the like. Preferred is benzyl.

"Aryloxy" means an oxy attached to the above "aryl", such as 1-naphthyloxy, 2-naphthyloxy, 1-anthryloxy, 2-anthryloxy, 9-anthryloxy, 1-phenanthryloxy, 2-phenanthryloxy, 3-phenanthryloxy, 4-phenanthryloxy, 9-phenanthryloxy, and the like. Preferred is phenyloxy or naphthyloxy (e.g., 1-napthyloxy, 2-naphthyloxy).

"Heterocyclic group" means "heteroring" or "heteroaryl".

"Heteroring" means a non-aromatic heterocyclic group (preferably 5- to 7-membered ring) which has at least one of nitrogen, oxygen, phosphorus and/or sulfur atoms in the ring and may be bonded at any substitutable position such as 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperadinyl, 2-piperadinyl, 2-morpholinyl, 3-morpholinyl, morpholino, tetrahydropyranyl, and the like. The "non-aromatic heterocyclic group" is a saturated or unsaturated ring.

"Heteroaryl" means a monocyclic aromatic heterocyclic group or a condensed aromatic heterocyclic group.

Monocyclic aromatic heterocyclic group means a group derived from a 5- to 8-membered aromatic ring optionally containing one to four of oxygen, sulfur, phosphorus and/or nitrogen atoms in the ring wherein the group may be bonded at any substitutable position.

Condensed aromatic heterocyclic group means a group wherein a 5- to 8-membered aromatic ring optionally containing one to four of oxygen, sulfur, phosphorus and/or nitrogen atoms in the ring is condensed with one to four of 5- to 8-membered aromatic carbocycle(s) or the other 5- to 8-membered aromatic heterocycle(s), and wherein the group may be bonded at any substitutable position.

Examples of "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl(e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl(e.g., 1-benzoimidazolyl, 2-benzoimidazolyl, 4-benzoimidazolyl, 5-benzoimidazolyl), dibenzofuryl, benzoxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), purinyl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl), phenothiazinyl (e.g., 1-phenothiazinyl, 2-phenothiazinyl, 3-phenothiazinyl, 4-phenothiazinyl), or the like.

"Heterocycle" and "heterocyclic ring" mean a ring from which the above heterocyclic group can be derived.

"Heterocyclic lower alkyl" and "heterocyclyl lower alkyl" mean lower alkyl substituted with the above "heterocyclic group".

"Heterocyclyloxy" means an oxy attached to the above "heterocyclic group".

"Lower alkoxy" or "alkoxy" mean an oxy attached to the above "lower alkyl" or "alkoxy", such as methoxy, ethoxy, n-propoxy, isopropoxy, n-butoxy, isobutoxy, tert-butoxy, and the like.

"Lower alkylcarbonyl", "cycloalkylcarbonyl", "cycloalkyl lower alkylcarbonyl", "lower alkoxycarbonyl", "arylcarbonyl", "aryl lower alkylcarbonyl", "aryloxycarbonyl", "heterocyclylcarbonyl", "heterocyclyl lower alkylcarbonyl", and "heterocyclyloxycarbonyl" means a carbonyl attached to the above "lower alkyl", "cycloalkyl", "cycloalkyl lower alkyl", "lower alkoxy", "aryl", "aryl lower alkyl", "aryloxy", "heterocyclic group", and "heterocyclyl lower alkyl", respectively.

When a substituent(s) is/are present on "optionally substituted lower alkyl", "optionally substituted cycloalkyl", "optionally substituted cycloalkyl lower alkyl", "optionally substituted lower alkenyl", "optionally substituted lower alkynyl", "optionally substituted lower alkoxy", "optionally substituted aryl", "optionally substituted aryl lower alkyl", "optionally substituted aryloxy", "optionally substituted heterocycle", "optionally substituted heterocyclic group", "optionally substituted heterocyclyl lower alkyl", "optionally substituted heterocyclyloxy", "optionally substituted lower alkenyloxy", "optionally substituted lower alkylcarbonyl", "optionally substituted cycloalkylcarbonyl", "optionally substituted cycloalkyl lower alkylcarbonyl", "optionally substituted lower alkoxycarbonyl", "optionally substituted arylcarbonyl", "optionally substituted aryl lower alkylcarbonyl", "optionally substituted aryloxycarbonyl", "optionally substituted heterocyclylcarbonyl", "optionally substituted heterocyclyl lower alkylcarbonyl", "optionally substituted heterocyclyloxycarbonyl", "optionally substituted lower alkylene", "optionally substituted lower alkenylene", "optionally substituted phosphoric acid residue", "optionally substituted carbocycle" or the like, each may be substituted with the same or different, 1 to 4 group(s) selected from Substituent group B and Substituent group A (described below) at any position.

Examples of Substituent group B include hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkenyl (e.g., vinyl), lower alkynyl (e.g., ethynyl), cycloalkyl (e.g., cyclopropyl), cycloalkenyl (e.g., cyclopropenyl), lower alkoxy, (e.g., methoxy, ethoxy, propoxy, butoxy), lower alkenyloxy (e.g., vinyloxy, allyloxy), lower alkoxycarbonyl (e.g., methoxycarbonyl, ethoxycarbonyl, tert-butoxycarbonyl), nitro, nitroso, optionally substituted amino (e.g., alkylamino (e.g., methylamino, ethylamino, dimethylamino), acylamino (e.g., acetylamino, benzoylamino), aralkylamino (e.g., benzylamino, tritylamino), hydroxyamino)), azido, aryl (e.g., phenyl), aralkyl (e.g., benzyl), cyano, isocyano, isocyanato, thiocyanato, isothiocyanato, mercapto, alkylthio (e.g., methylthio), alkylsulfonyl (e.g., methanesulfonyl, ethansulfonyl), optionally substituted alkylsulfonylamino (e.g., methanesulfonylamino, ethanesulfonylamino, N-methylsulfonyl-N'-methylamino), optionally substituted carbamoyl (e.g., alkylcarbamoyl (e.g., methylcarbamoyl, ethylcarbamoyl, dimethylcarbamoyl)), sulfamoyl, acyl (e.g., formyl, acetyl), formyloxy, haloformyl, oxalo, thioformyl, thiocarboxy, dithiocarboxy, thiocarbamoyl, sulfino, sulfo, sulfoamino, hydrazino, azido, ureido, amidino, guanidino, phthalimido, oxo, phosphoric acid residue, phosphoric-acid-residue-substituted lower alkyl (which may be intervened by a heteroatom group(s)), aryl substituted with a phosphoric acid residue, aralkyl substituted with a phosphoric acid residue, hydroxy lower alkyl and the like, more preferably hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkoxy (e.g., methoxy, ethoxy, propoxy, butoxy), optionally substituted amino (e.g., alkylamino (e.g., methylamino, ethylamino, dimethylamino), oxo, phosphoric acid residue, and the like.

Examples of a substituent(s) of "optionally substituted amino" or "optionally substituted carbamoyl" include mono- or di-lower alkyl, lower alkylcarbonyl, or lower alkylsulfonyl, optionally substituted lower alkyl (e.g., methyl, ethyl, isopropyl, benzyl, carbamoylalkyl (e.g., carbamoylmethyl), mono- or di-lower alkylcarbamoyl lower alkyl (e.g., dimethylcarbamoylethyl), hydroxy lower alkyl, heterocyclyl lower alkyl (e.g., morpholinoethyl, tetrahydropyranylethyl), alkoxycarbonyl lower alkyl(e.g., ethoxycarbonylmethyl, ethoxycarbonylethyl), mono- or di-lower alkylamino lower alkyl (e.g., dimethylaminoethyl)) lower alkoxy lower alkyl (e.g., methoxyethyl, ethoxymethyl, ethoxyethyl, isopropoxyethyl, and the like), acyl (e.g., formyl, optionally substituted lower alkylcarbonyl (e.g., acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl), lower alkoxy lower alkylcarbonyl (e.g., methoxyethylcarbonyl), lower alkylcarbamoyl lower alkylcarbonyl (e.g., methylcarbamoylethylcarbonyl), alkoxycarbonylacetyl), optionally substituted arylcarbonyl (e.g., benzoyl, toluoyl), optionally substituted aralkyl (e.g., benzyl, 4-fluorobenzyl), hydroxy, optionally substituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl), arylsulfonyl optionally substituted with lower alkyl or halogen (e.g., benzenesulfonyl, toluenesulfonyl, 4-fluorobenzenesulfonyl), cycloalkyl (e.g., cyclopropyl), aryl optionally substituted with lower alkyl (e.g., phenyl, trityl), lower alkylaminosulfonyl (e.g., methylaminosulfonyl, dimethylaminosulfonyl), lower alkylaminocarbonyl (e.g., dimethylaminocarbonyl), lower alkoxycarbonyl (e.g., ethoxycarbonyl), cycloalkylcarbonyl (e.g., cyclopropylcarbonyl, cyclohexylcarbonyl), optionally substituted sulfamoyl (e.g., sulfamoyl, methylsulfamoyl, dimethylsulfamoyl), lower alkylcarbonylamino (e.g., methylcarbonylamino), heterocycle (e.g., morpholino, tetrahydropyranyl), optionally substituted amino (e.g., mono- or di-alkylamino (e.g., dimethylamino), formylamino), and the like.

As to an amino group of "optionally substituted amino", "optionally substituted aminocarbonyl", or "optionally substituted carbamoyl", two substituents on the amino group together with the adjacent nitrogen atom may form a nitrogen-containing heterocycle which may contains sulfur and/or oxygen atoms in the ring (preferably 5- to 7-membered ring, also preferably saturated ring) and the ring is optionally substituted with oxo or hydroxy. The sulfur atom forming the ring may be substituted with oxo. A 5- or 6-membered ring and the like such as piperazinyl, piperidino, morpholino, pyrrolidino, 2-oxopiperidino, 2-oxopyrrolidino, 4-hydroxymorpholino and the like are preferred.

"Phosphoric acid residue" means a group represented by the formula: —$PO(OH)_2$. "Optionally substituted phosphoric acid residue" means a phosphoric acid residue in which the OH part and/or hydrogen of the OH may be substituted.

More Preferred Embodiments

Q is a group selected from the following group:
$Q^1$: a carbocyclic group that is optionally substituted and optionally condensed; and
$Q^2$: a heterocyclic group that is optionally substituted and optionally condensed.
Q is preferably $Q^2$: a heterocyclic group that is optionally substituted.

Q is more preferably a 5- to 7-membered monocyclic heterocyclic group that is optionally substituted and contains one to four heteroatoms that are one or the same or different, two or more heteroatoms selected from O, S, and N atoms. Q is, further preferably, a monocyclic aromatic heterocyclic group containing one to three of the heteroatoms, particularly preferably, a 5-membered ring, and most preferably, a 5-membered monocyclic aromatic heterocyclic group containing one S atom and one or two N atoms. Preferred Q is, specifically, a ring shown below:

[Chemical formula 9]

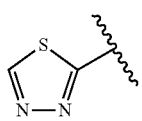
(1)

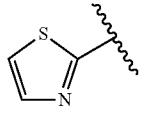
(2)

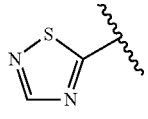
(3)

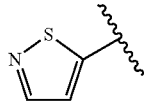
(4)

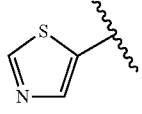
(5)

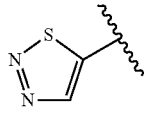
(6)

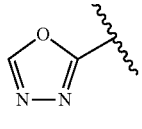
(7)

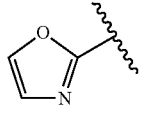
(8)

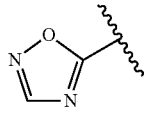
(9)

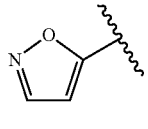
(10)

-continued

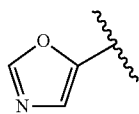
(11)

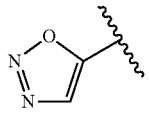
(12)

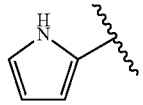
(13)

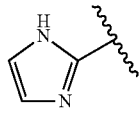
(14)

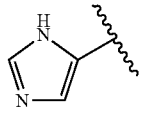
(15)

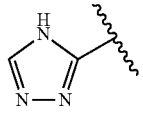
(16)

Q is, more preferably, a ring of the above-described (1), (2), (3), (5), (7), (8), (11), (13), (14), (15), or (16), particularly preferably a ring of the above-described (1), (2), (3), or (5), and most preferably a ring of the above-described (1) or (2).

Examples of a condensed ring of the above-described monocyclic heterocyclic group include a benzene ring and other monocyclic heterocycle (preferably 5- to 7-membered).

A substituent(s) in the "optionally substituted" on Q is more preferably the same or different, one to four, further preferably one or two, substituent(s) selected from Substituent group A.

Substituent group A: lower alkyl (e.g., methyl, ethyl), lower alkoxy (e.g., methoxy, ethoxy), halogen (e.g., F, Br), halogenated lower alkyl (e.g., —CH$_2$F, —CHF$_2$, —CF$_3$, —CH$_2$CH$_2$F, —CH$_2$CHF$_2$, —CH$_2$CF$_3$), halogenated lower alkoxy (e.g., —OCH$_2$F, —OCHF$_2$, —OCF$_3$, —OCH$_2$CH$_2$F, —OCH$_2$CHF$_2$, —OCH$_2$CF$_3$), and a group represented by the formula:

[Chemical formula 10]

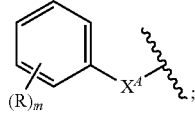
(B)

in the above formula,
X$^A$ is a group selected from the following group:
X$^{A1}$: a single bond;
X$^{A2}$: a group selected from C=O and C=S;
X$^{A3}$: a heteroatom group selected from O, S, SO, SO$_2$, and NR$^{1'}$ wherein R$^{1'}$ is hydrogen or lower alkyl;

$X^{A4}$: a group formed by linking the same or different, two or more groups selected from $X^{A2}$ and $X^{A3}$ (e.g. —CONH—, —CONHNH—, —CONHNHCO—, —CONHO—, —CONHNHSONH—, —CONHNMe-, —NHCONH—, —NHCOO—);

$X^{A5}$: a group selected from —N=N—, —C(R$^{1'}$)=N—, or —N=C(R$^{1'}$)— wherein R$^{1'}$ is hydrogen or lower alkyl;

$X^{A6}$: optionally substituted lower alkylene or optionally substituted lower alkenylene (example of substituent: methyl, phenyl);

$X^{A7}$: $X^{A6}$ intervened by one or any two or more groups selected from $X^{A2}$, $X^{A3}$, $X^{A4}$, and $X^{A5}$ (e.g., —CONHCH$_2$—, —CONMeCH$_2$—, —CONHCH$_2$CH$_2$O—, —CONHCH$_2$CH$_2$—SO$_2$—, —CONHCH$_2$CH$_2$CH$_2$—); and $X^{A8}$: a spacer consisting of any combination of $X^{A1}$ to $X^{A7}$.

In $X^A$, "intervene" may be any of cases where one or any two or more groups selected from $X^{A2}$, $X^{A3}$, $X^{A4}$ and $X^{A5}$ 1) are present between carbon atoms constituting lower alkylene or lower alkenylene, 2) are present at an end of lower alkylene or lower alkenylene, and where 1) and 2) coexist.

$X^A$ is a spacer consisting of, preferably, one to five atoms linked, and more preferably, one to three atoms linked. $X^A$ is more preferably lower alkylene, and further preferably C1-C3 alkylene.

R is a group independently selected from the following group:
(1) lower alkyl,
(2) lower alkoxy,
(3) halogen,
(4) halogenated lower alkyl,
(5) halogenated lower alkoxy, and
(6) lower cycloalkyl.

m is an integer of 0 to 5.

R is, preferably, independently lower alkoxy, halogen, or halogenated lower alkyl, and more preferably halogen.

Q is more preferably substituted with a group shown in the above-described (B).

m is preferably 1 or 2.

R$^3$ may be a variety of substituents as far as they do not adversely affect on the pharmacological activity of the present compound. Examples thereof include, for example, hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, an optionally substituted heterocyclic group, an optionally substituted heterocyclyloxy group, and optionally substituted amino. Examples of a substituent(s) in the "optionally substituted" include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclic group, lower alkylcarbonyl, lower alkylcarbonyloxy, lower alkoxycarbonyl, halogenated lower alkyl, halogenated lower alkoxy, and the like. More preferred are halogen, hydroxy, amino, lower alkylamino, lower alkyl, lower alkoxy, and the like. R$^3$ is more preferably hydrogen, halogen, hydroxy, lower alkyl, lower alkenyl, lower alkoxy, lower alkenyloxy, or optionally substituted amino, further preferably hydrogen or lower alkyl (e.g., methyl), and particularly preferably hydrogen.

The A ring is an optionally substituted heterocycle containing at least one N atom. The heterocycle is preferably a 5- to 7-membered ring containing one to three, preferably two or three, O, S and/or N atoms, and more preferably is selected from the foregoing heterocycles. One of preferred embodiments of the A ring is an optionally substituted ring described below:

[Chemical formula 11]

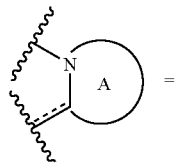 =

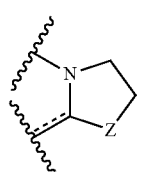 (a)

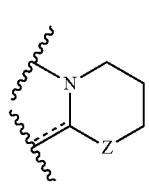 (b)

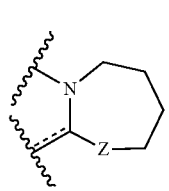 (c)

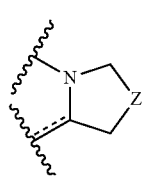 (d)

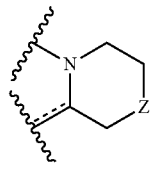 (e)

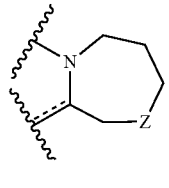 (f)

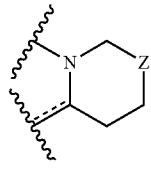 (g)

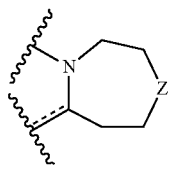

(h)

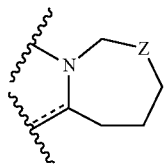

(i)

wherein Z is $CH_2$, O, S, SO, $SO_2$, or $NR^{19}$.

The A ring is preferably a ring of (a), (b) or (c), more preferably a ring of (a) or (b), and particularly preferably a ring of (b).

One of preferred embodiments of Z is O or $NR^{19}$, and O is more preferred.

When Z=$NR^{19}$, $R^{19}$ is preferably, 1) hydrogen, 2) optionally substituted lower alkyl (example of substituent: amino optionally substituted with mono- or di-lower alkyl, cycloalkyl, hydroxy, an optionally substituted heterocyclic group (wherein the heterocycle is preferably a 5- to 7-membered ring; example: furyl, thienyl, thiazolyl, pyridyl, morpholino, imidazole; example of substituent: lower alkyl, halogen), optionally substituted heterocyclylcarbonyl (wherein the heterocycle is preferably a 5- to 7-membered ring; example: morpholinocarbonyl), optionally substituted phenyl (substituent: lower alkyl, amino, lower alkylamino, hydroxy, halogen, halogenated lower alkyl, lower alkoxy, halogenated lower alkoxy, lower alkylthio, lower alkylsulfonyl), acetylamino, carbamoyl, mono- or di-lower alkyl-substituted carbamoyl, lower alkylsulfonylamino, lower alkoxy, carbonyl, halogen, thiol, lower alkylthio), 3) lower alkenyl, 4) acyl (e.g., lower alkylcarbonyl), or 5) lower alkylsulfonyl. $R^{19}$ may be selected from the Substituent group S2 described below.

Another substituent on the A ring may be selected from $R^{15}$ to $R^{18}$ or the Substituent group S2 described below, and is preferably lower alkyl. Alternatively, a substituent part on the A ring may form a ring such as condensed ring, Spiro ring, or the like, as described below. In this case, the present compound encompasses a tetracyclic compound.

The A ring is more preferably any of the following rings:

[Chemical formula 12]

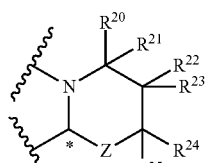

(A-1)

Z = O or $NR^{26}$

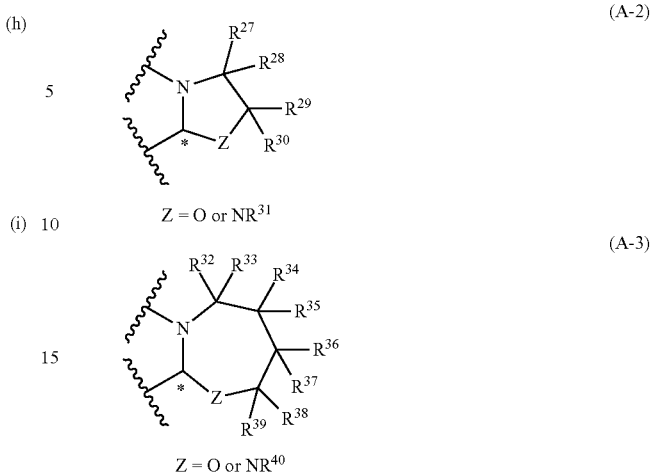

and further preferably (A-1),
wherein each of $R^{20}$ to $R^{40}$ is independently a group selected from the Substituent group S2 described below, or any two groups of $R^{20}$ to $R^{40}$ that are attached to the same atom may be taken together with the atom to form a spiro ring (e.g., an optionally substituted carbocycle or an optionally substituted heterocycle), or each combination of ($R^{20}$ and $R^{22}$), ($R^{23}$ and $R^{24}$), ($R^{25}$ and $R^{26}$), ($R^{27}$ and $R^{29}$), ($R^{30}$ and $R^{31}$), ($R^{32}$ and $R^{34}$), ($R^{35}$ and $R^{36}$), ($R^{37}$ and $R^{38}$), and ($R^{39}$ and $R^{40}$) may be taken together with the adjacent atom to form an optionally substituted carbocycle or an optionally substituted heterocycle.

Substituent group S2: hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, an optionally substituted heterocyclic group, optionally substituted heterocyclyl lower alkyl, optionally substituted heterocyclyloxy, hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, $SO_2$, $NR^5$ (wherein $R^5$ is, independent of $R^4$, selected from the same substituent group as $R^4$), —N=, and =N—).

The stereochemistry of an asymmetric carbon indicated by * is R- or S-configuration, or a mixture thereof.

In one embodiment, $R^{20}$ to $R^{40}$ are each independently, preferably, hydrogen, optionally substituted lower alkyl (example of substituent: OH, lower alkoxy, cycloalkyl, lower alkylthio, lower alkylsulfonyl, heterocyclic group, aryl, optionally substituted amino (example of substituent: lower alkyl, acyl)) cycloalkyl, optionally substituted aryl (example of substituent: OH, lower alkyl), or an optionally substituted heterocyclic group.

In one embodiment, $R^{20}$ to $R^{25}$, $R^{27}$ to $R^{30}$, and $R^{32}$ to $R^{39}$ are each, preferably, hydrogen, $C_1$-$C_8$ alkyl, $C_6$-$C_{14}$ aryl $C_1$-$C_8$ alkyl, $C_6$-$C_{14}$ aryl or alkoxy.

In one embodiment, $R^{26}$, $R^{31}$ and $R^{40}$ are each independently, preferably, hydrogen; $C_{3-6}$ cycloalkyl; a heterocycle; or $C_{1-8}$ alkyl optionally substituted with hydroxy, $C_{3-6}$ cycloalkyl, alkoxy, heteroaryl, $C_{6-14}$ aryl, or amino wherein the amino may be substituted with —C(O)$C_{1-8}$ alkyl or $C_{1-8}$ alkyl.

More preferred embodiments are illustrated below.

I) When the A ring is (A-1), preferably, 1) Z is $NR^{26}$, $R^{26}$ and $R^{24}$ are taken together to form a heterocycle, and the others are hydrogen; 2) Z is O or $NR^{26}$, ($R^{20}$ and $R^{22}$) or ($R^{23}$ and $R^{24}$) are taken together to form cycloalkyl substituted with phenyl, and the others are hydrogen or optionally substituted lower alkyl; 3) Z is O, $R^{20}$ or $R^{21}$ is lower alkyl, and the others are hydrogen.

II) When the A ring is (A-2), preferably, 1) Z is O, $R^{27}$ or $R^{28}$ is lower alkyl, the others are hydrogen; 2) Z is $NR^{31}$, $R^{30}$ and $R^{31}$ are taken together to form a heterocycle, the others are hydrogen, or $R^{27}$ and $R^{29}$ are taken together to form cycloalkyl, and the others are hydrogen; 3) Z is O, $R^{27}$ and $R^{29}$ are taken together to form cycloalkyl optionally condensed to phenyl, and the others are hydrogen.

$R^{14}$ and $R^x$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, an optionally substituted heterocyclic group, optionally substituted heterocyclyl lower alkyl, optionally substituted heterocyclyloxy, hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, optionally substituted phosphoric acid residue, aryl optionally substituted with optionally substituted phosphoric acid residue, aralkyl optionally substituted with optionally substituted phosphoric acid residue, hydroxy optionally substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of O, S, SO, $SO_2$, $NR^a$ (wherein $R^a$ is hydrogen or lower alkyl), —N=, and =N—).

$R^{14}$ and $R^x$ are each independently, preferably, hydrogen, hydroxy, optionally substituted lower alkyl (wherein the substituent is preferably, for example, amino, lower alkyl, lower alkylamino, hydroxy, or lower alkoxy). $R^{14}$ and $R^x$ are preferably hydrogen.

The broken line in Compound (I-1) represents the presence or absence of a bond; with the proviso that when the broken line represents the presence of a bond, $R^X$ is not present.

In Compound (I-2), the D ring means the same heterocycle as the A ring, and a 5- to 7-membered ring is preferred. A substituent(s) on the D ring is the same as that on the A ring. The other symbols are as defined above.

In Compound (I-3), each group is as described below.

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, an optionally substituted heterocyclic group, an optionally substituted heterocyclyloxy group, or optionally substituted amino. More preferred is hydrogen or optionally substituted lower alkyl.

$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, an optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of O, S, SO, $SO_2$, $NR^a$ (wherein $R^a$ is hydrogen or lower alkyl), —N= and =N—). More preferred is hydrogen, optionally substituted lower alkyl, optionally substituted cycloalkyl, optionally substituted cycloalkyl lower alkyl, optionally substituted lower alkenyl, optionally substituted aryl, optionally substituted aryl lower alkyl, an optionally substituted heterocyclic group, or optionally substituted heterocyclyl lower alkyl.

The broken line represents the presence or absence of a bond.

Either one of $B^1$ and $B^2$ is $CR^{20}R^{21}$, and the other is $NR^{22}$. In this case, the broken line is not present.

When $B^2$ is $NR^{22}$, $R^4$ and $R^{22}$ may be taken together to form an optionally substituted heterocycle (e.g., G ring).

When $B^2$ is $CHR^{21}$, $R^4$ and $R^{21}$ may be taken together to form an optionally substituted heterocycle (e.g., H ring).

Alternatively, $B^1$ and $B^2$ are each independently $CR^{23}$ or N. In this case, the broken line represents the presence of a bond, and/or $B^1$ and $B^2$ parts are taken together to form an optionally substituted heterocycle (e.g., C ring).

$R^{20}$, $R^{21}$, $R^{22}$ and $R^{23}$ are each independently selected from hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, an optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of O, S, SO, $SO_2$, $NR^5$ (wherein $R^5$ is, independent of $R^4$, selected from the same substituent group as $R^4$), —N═, and ═N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, substituted (thio)urea, or substituted sulfonyl.

$R^{20}$, $R^{21}$, $R^{22}$, and $R^{23}$ are more preferably selected from hydrogen, optionally substituted lower alkyl, optionally substituted cycloalkyl, optionally substituted cycloalkyl lower alkyl, optionally substituted aryl, optionally substituted aryl lower alkyl, an optionally substituted heterocyclic group, optionally substituted heterocyclyl lower alkyl, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, substituted (thio)urea, or substituted sulfonyl.

The above-described Compound (I-3) encompasses compound described below.

[Chemical formula 13]

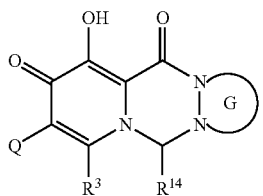

(I-3-1)

The G ring is a 5- to 7-membered ring containing two or three O, S and/or N atoms, and contains at least two N atoms. More preferably, it is selected from the foregoing heterocycle, and the following rings are illustrated;

[Chemical formula 14]

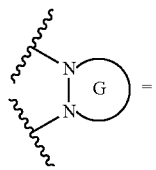

(a)

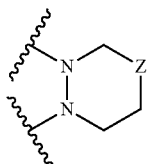

(b)

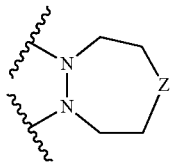

(c)

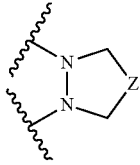

(d)

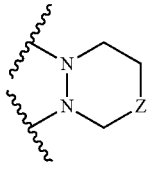

(e)

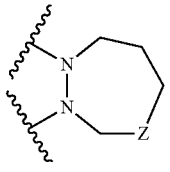

(f)

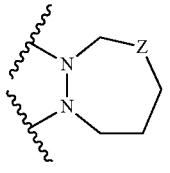

(g)

wherein Z is $CH_2$, O, S, SO, $SO_2$, or $NR^{19}$.

Examples of a substituent(s) on the G ring include the same or different, one or more substituents selected from the foregoing Substituent group S2. Alternatively, the substituent part on the G ring may be taken together with the adjacent atom to further form a condensed ring or a spiro ring, preferably an optionally substituted carbocycle (preferably 5- to 6-membered ring) or an optionally substituted heterocycle (preferably 5- to 6-membered ring).

One of preferred embodiments of a substituent(s) on the G ring is lower alkyl (e.g., isopropyl), lower alkoxy lower alkyl (e.g., 2-methoxyethyl), optionally substituted amino (example of substituent: lower alkyl (e.g., methyl), or lower alkylcarbonyl (e.g., acetyl)).

$R^3$ is preferably hydrogen or optionally substituted lower alkyl; and more preferably hydrogen.

Examples of $R^{14}$ include the same groups as in the cases of $R^{20}$, $R^{21}$, $R^{22}$, and $R^{23}$ described above. However, $R^{14}$ is preferably hydrogen, optionally substituted lower alkyl (substituent: amino, lower alkylamino, lower alkoxy, aryloxy, cyano, halogen, (substituted) carbamoyl, acylamino, lower alkynyl, hydroxy), cycloalkyl, cycloalkyl lower alkyl, phenyl, benzyl, 5- to 6-membered aromatic heterocyclic group, 5- to 6-membered heterocyclyl lower alkyl, optionally substituted lower alkylcarbonyl (substituent: lower alkoxy), optionally substituted benzoyl (substituent: lower alkoxy), substituted sulfonyl(substituent: lower alkyl, aryl, heterocyclic group); and more preferably hydrogen or optionally substituted lower alkyl.

[Chemical formula 15]

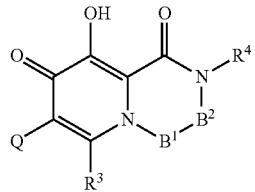

(I-3-2)

Preferably, $B^1$ is $CR^{20}R^{21}$ and $B^2$ is $NR^{22}$ wherein $R^{20}$, $R^{21}$, and $R^{22}$ are defined the same as above.

Alternatively, preferably, $B^1$ is $NR^{22}$ and $B^2$ is $CR^{20}R^{21}$ wherein $R^{20}$, $R^{21}$, and $R^{22}$ are defined the same as above.

When $B^2$ is $NR^{22}$, $R^4$ and $R^{22}$ may be taken together to form an optionally substituted heterocycle (e.g., the above-described G ring);

When $B^2$ is $CR^{20}R^{21}$, $R^4$ and $R^{21}$ may be taken together to form an optionally substituted heterocycle;

$R^3$ is preferably hydrogen or optionally substituted lower alkyl; and more preferably hydrogen.

$R^{20}$, $R^{21}$ and $R^{22}$ are preferably each independently, hydrogen, optionally substituted lower alkyl (example of substituent: amino, lower alkylamino, lower carbonylamino, lower alkoxy, aryloxy, cyano, halogen, acylamino(e.g., lower carbonylamino), lower alkynyl, hydroxy, lower alkoxycarbonyl, optionally substituted heterocyclylcarbonyl (example of substituent: lower alkyl, lower alkoxy), lower alkenyl, optionally substituted carbamoyl (example of substituent: lower alkyl), lower alkylcarbonyloxy, lower alkyloxycarbonyl, lower alkylcarbonylamino, oxo, lower alkynyl), cycloalkyl, cycloalkyl lower alkyl, optionally substituted aryl (example of substituent: lower alkyl, halogen, lower alkyloxy, nitro), optionally substituted aryl lower alkyl (example of substituent: lower alkyl, halogen, lower alkyloxy, nitro, oxo), an optionally substituted heterocyclic group (example of substituent: lower alkyl, halogen, lower alkyloxy, nitro), optionally substituted heterocyclyl lower alkyl (example of substituent: lower alkyl, halogen, lower alkyloxy, nitro, oxo), optionally substituted lower alkylcarbonyl (substituent: lower alkoxy, halogen), cycloalkyl carbonyl, optionally substituted benzoyl (substituent: lower alkoxy, halogen), or substituted sulfonyl (substituent: lower alkyl, aryl, heterocyclic group (preferably 5- to 6-membered aromatic heterocyclic group)).

More preferably, $R^{20}$ and $R^{21}$ are both hydrogen.

In Compound (I-3-2), more preferably, $X^A$ is lower alkylene; $R^3$ is hydrogen; $B^1$ is $CH_2$ or $NR^{22}$; $B^2$ is $NR^{22}$ or $CH_2$; and more preferably $B^1$ is $NR^{22}$; and $B^2$ is $CH_2$.

$R^4$ is, preferably, optionally substituted lower alkyl (e.g., methyl, ethyl, n-propyl, i-propyl, n-butyl; example of substituent: hydroxy, amino, lower alkylamino, lower alkoxy, aryloxy, oxo, lower alkoxycarbonyl, optionally substituted heterocyclylcarbonyl (example of substituent: lower alkyl, lower alkoxy)), specifically, lower alkylamino lower alkyl (e.g., 2-dimethylaminoethyl, 2-diethylaminoethyl), lower alkoxy lower alkyl (e.g., 1-methoxyethyl, 2-methoxypropyl, 2-methoxyethyl, 3-methoxypropyl, 4-methoxybutyl, 2-ethoxyethyl, 3-ethoxypropyl, 4-ethoxybutyl, 2-propoxyethyl, 3-propoxypropyl, 4-propoxybutyl) or aryloxy lower alkyl (e.g. 2-phenoxyethyl, 3-phenoxypropyl); optionally substituted cycloalkyl (e.g., cyclopropyl); optionally substituted cycloalkyl lower alkyl (e.g., cyclopropylmethyl, 1-adamantylmethyl, 2-adamantylmethyl, dodecahedranemethyl, cubanemethyl); optionally substituted aryl (e.g., phenyl; example of substituent: lower alkyl, halogen, lower alkyloxy, nitro; or a substituent part may be lower alkylene that may be intervened by a heteroatom (e.g., O)); optionally substituted aryl lower alkyl (e.g., benzyl; example of substituent: lower alkyl, halogen, lower alkyloxy, nitro; or a substituent part may be lower alkylene that may be intervened by a heteroatom (e.g., O)); an optionally substituted heterocyclic group (preferably 5- to 6-membered ring) (e.g., picolyl, pyridyl; example of substituent: lower alkyl, halogen, lower alkyloxy, nitro); or an optionally substituted heterocyclic group (preferably 5- to 6-membered ring) lower alkyl (e.g., piperonylmethyl, 2-morpholinoethyl, thiophenemethyl, furanmethyl, tetrahydrofuranmethyl, dioxanemethyl, tetrahydropyranmethyl, thiazolemethyl, oxazolemethyl, 1,2,4-oxadiazolemethyl, 1,3,4-oxadiazolemethyl; example of substituent: lower alkyl, halogen, lower alkyloxy, nitro; and the heterocycle may be condensed to a benzene ring).

$R^{22}$ is, preferably, optionally substituted alkyl (e.g., methyl, ethyl, n-propyl, i-propyl, n-butyl, neopentyl; example of substituent: amino, lower alkyl amino, lower alkoxy, aryloxy, cyano, halogen, (substituted)carbamoyl, acylamino, oxo), specifically, lower alkylamino lower alkyl (e.g., 2-dimethylaminoethyl, 2-diethylaminoethyl), lower alkoxy lower alkyl (e.g., 1-methoxyethyl, 2-methoxypropyl, 2-methoxyethyl, 3-methoxypropyl, 4-methoxybutyl, 2-ethoxyethyl, 3-ethoxypropyl, 4-ethoxybutyl, 2-propoxyethyl, 3-propoxypropyl, 4-propoxybutyl), aryloxy lower alkyl (e.g., 2-phenoxyethyl, 3-phenoxypropyl), cyano lower alkyl (e.g., cyanomethyl), halogenated lower alkyl (e.g., fluoromethyl, 2,2,2-trifluoromethyl), or carboranemethyl, acylamino lower alkyl (e.g., 2-acetamidoethyl); lower alkenyl (e.g., allyl, propargyl, crotyl); cycloalkyl lower alkyl (e.g., 3-cyclopropyl, cyclopropylmethyl, 1-adamantylmethyl, 2-adamantylmethyl, dodecahedranemethyl, cubanemethyl); optionally substituted aryl (e.g., phenyl; a substituent part may be lower alkylene that may be intervened by a heteroatom (e.g., O)); optionally substituted aryl lower alkyl (e.g. benzyl; a substituent part may be lower alkylene that may be intervened by a heteroatom (e.g., O)); an optionally substituted heterocyclic group (e.g., picolyl, pyridyl; example of substituent: lower alkyl); optionally substituted heterocyclyl lower alkyl (e.g., piperonylmethyl, morpholinoethyl, furanmethyl, tetrahydropyranmethyl, dioxanemethyl, tetrahydropyranmethyl, triazolemethyl, tetrazolemethyl, thiazolemethyl, oxazolemethyl, 1,2,4-oxadiazolemethyl 1,3,4-oxadiazolemethyl isoxazolemethyl, imidazolemethyl, methylpyrrolemethyl, 18-crown ether methyl; example of substituent: lower alkyl); optionally substituted lower alkylcarbonyl (e.g., acetyl; example of substituent: lower alkoxy (e.g., methoxy)); optionally substituted aryl carbonyl (e.g., benzoyl; example of substituent: lower alkoxy); substituted (thio)urea (e.g., urea, lower alkylurea (e.g., dimethylurea), dimethylthiourea); or substituted sulfonyl (e.g., alkylsulfonyl (e.g., methanesulfonyl), aryl sulfonyl (e.g., benzenesulfonyl), heterocyclyl sulfonyl (e.g., thiophenesulfonyl)).

[Chemical formula 16]

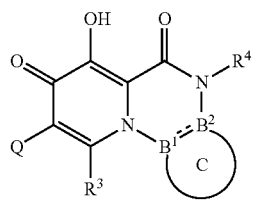

(I-3-3)

The C ring represents an optionally substituted heterocycle or an optionally substituted carbocycle. $B^1$ and $B^2$ are each independently C, $CR^{23}$, or N; with the proviso that when $B^1$ and $B^2$ are each independently $CR^{23}$ or N, the broken line represents the absence of a bond. Examples of the C ring include the same heterocycle as those of the A ring and the G ring, and examples of a substituent(s) on the C ring similarly include. That is, examples of a substituent(s) on the C ring include the same or different, one or more substituents selected from the foregoing Substituent group S2. Alternatively, a substituent part on the C ring may be taken together with the adjacent atom to further form a condensed ring or a spiro ring, preferably, an optionally substituted carbocycle (preferably 5- to 6-membered ring) or an optionally substituted heterocycle (preferably 5- to 6-membered ring).

When the C ring is a carbocycle, $B^1$ and $B^2$ are each independently C or CH. Examples of the carbocycle include 5- to 7-membered rings.

The broken line represents the presence or absence of a bond, and preferably represents the absence.

The C ring encompasses the following rings:

[Chemical formula 17]

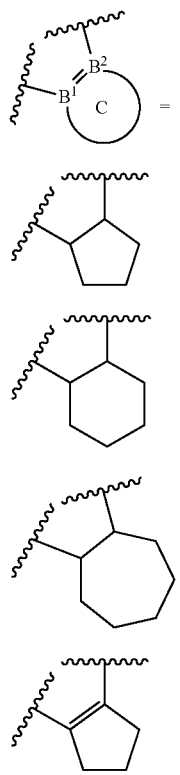

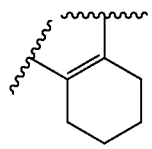
(e)

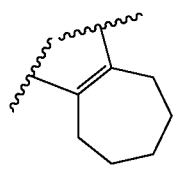
(f)

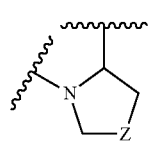
(g)

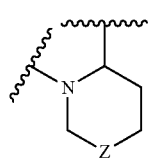
(h)

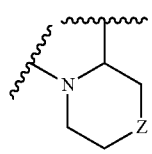
(i)

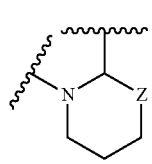
(j)

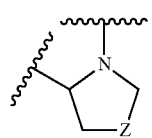
(k)

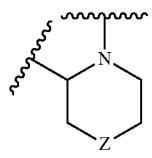
(l)

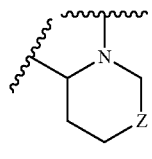
(m)

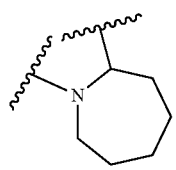
(n)

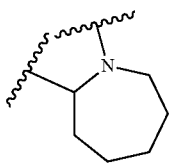

(o)

wherein Z is $CH_2$, O, S, SO, $SO_2$, or $NR^{19}$.

One of preferred embodiments as a substituent (s) on the C ring is lower alkyl (e.g., methyl, isopropyl), lower alkoxy lower alkyl (e.g., 2-methoxyethyl), optionally substituted amino (example of substituent: lower alkyl (e.g., methyl), lower alkylcarbonyl (e.g., acetyl)).

$R^{19}$ is more preferably hydrogen, lower alkyl, or lower alkoxy lower alkyl.

$R^3$ is preferably hydrogen or optionally substituted lower alkyl, and more preferably hydrogen.

In Compound (I-3-3), examples of $R^4$ include, preferably, the same groups as $R^4$ of Compound (I-3-2).

[Chemical formula 18]

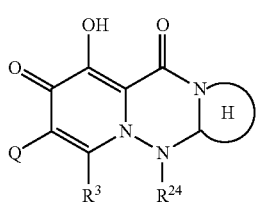

(I-3-4)

The H ring means the heterocycle defined the same as the A ring, and preferably is a 5- to 7-membered ring. Also, examples of a substituent(s) on each ring include the same substituent as in the case of the A ring. That is, examples of a substituent(s) on the H ring include the same or different, one or more substituents selected from the foregoing Substituent group S2. Alternatively, a substituent part on the H ring may be taken together with the adjacent atom to further form a condensed ring or a spiro ring, preferably, an optionally substituted carbocycle (preferably 5- to 6-membered ring) or an optionally substituted heterocycle (preferably 5- to 6-membered ring).

$R^3$ is preferably hydrogen or optionally substituted lower alkyl; and more preferably hydrogen.

Examples of $R^{24}$ include the same groups as in the case of $R^{20}$, $R^{21}$, $R^{22}$, and $R^{23}$ described above. However, it is preferably hydrogen, optionally substituted lower alkyl (substituent amino, lower alkylamino, lower alkoxy, aryloxy, cyano, halogen, (substituted) carbamoyl, acylamino, lower alkynyl, hydroxy), cycloalkyl, cycloalkyl lower alkyl, phenyl, benzyl, 5- to 6-membered aromatic heterocyclic group, 5- to 6-membered heterocyclyl lower alkyl, optionally substituted lower alkylcarbonyl (substituent: lower alkoxy, halogen), optionally substituted benzoyl (substituent: lower alkoxy, halogen), or substituted sulfonyl (substituent: lower alkyl, aryl, heterocyclic group (preferably 5- to 6-membered aromatic heterocyclic group)); and more preferably hydrogen or optionally substituted lower alkyl.

The present compound has at least the following characteristics as its chemical structure:
(1) the condensed heterocycle, which is the main backbone, is substituted with oxo (=O), hydroxy (OH), and oxo (=O); and
(2) an adjacent position to oxo on the condensed heterocycle has a cyclic group represented by -Q. Q is preferably an optionally substituted heterocyclic group.

By possession of such a structure, the present compound exhibits remarkably potent integrase inhibitory activity and/or cell proliferation inhibitory activity against viruses including HIV (preferably HIV-1). Preferably, it is also effective against resistant bacteria. Meanwhile, the structures of other parts ($R^3$, $R^{14}$, $R^X$, A ring, D ring, $B^1$, $B^2$, G ring, C ring, H ring, etc.) can be relatively freely selected from various structures, may have any kind of substituent, may form a condensed ring, and the condensed ring may be further substituted.

The present invention also provides pharmaceutically acceptable salts of the above-described compound, and solvates thereof. All theoretically possible tautomers, geometrical isomers, stereoisomers, optical isomers, racemates, and the like of the present compound are also within the scope of the invention.

Pharmaceutically acceptable salts of a compound of the present invention include, as basic salts, for example, alkali metal salts such as sodium salts, potassium salts, and the like; alkaline-earth metal salts such as calcium salts, magnesium salts, and the like; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts, ethylenediamine salts, and the like; aralkylamine salts such as N,N-dibenzylethylenediamine salts, benethamine salts, and the like; heterocyclic aromatic amine salts such as pyridine salts, picoline salts, quinoline salts, isoquinoline salts, and the like; quaternary ammonium salts such as tetramethylammonium salts, tetraethylammonium salts, benzyltrimethylammonium salts, benzyltriethylammonium salts, benzyltributylammonium salts, methyltrioctylammonium salts, tetrabutylammonium salts, and the like; basic amino acid salts such as arginine salts, lysine salts, and the like; and the like. Acid salts thereof include, for example, inorganic acid salts such as hydrochlorides, sulfates, nitrates, phosphates, carbonates, hydrogen carbonates, and perchlorates, and the like; organic acid salts such as acetates, propionates, lactates, maleates fumarates, tartrates, malates, citrates, ascorbates, and the like; sulfonates such as methanesulfonates isethionates, benzenesulfonates p-toluenesulfonates, and the like; acidic amino acid salts such as aspartates, glutamates, and the like; and the like.

Solvates of a compound of the present invention include solvates with alcohol, hydrates, and the like.

The compounds of the present invention can be synthesized using commercially available reagents and known compounds as raw materials, preferably by or in accordance with the following method. Although synthesis methods will be explained taking Compounds (I-1) and (I-3) as examples, other compounds of the present invention can be synthesized in a similar manner.

(Production Method 1)

[Chemical formula 19]

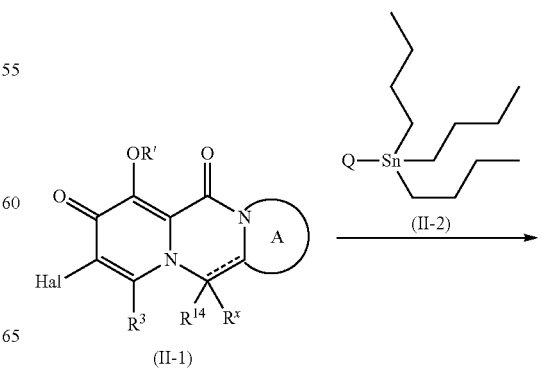

-continued

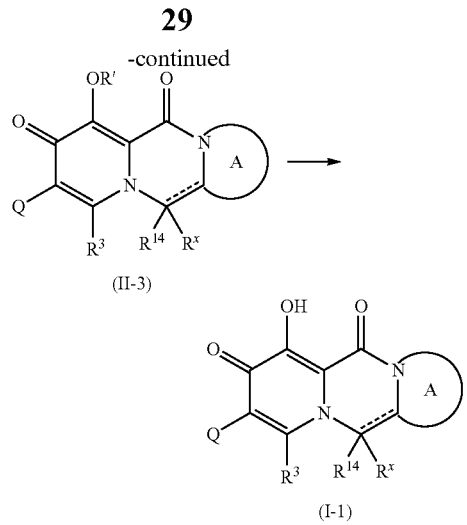

(Production Method 2)

[Chemical formula 20]

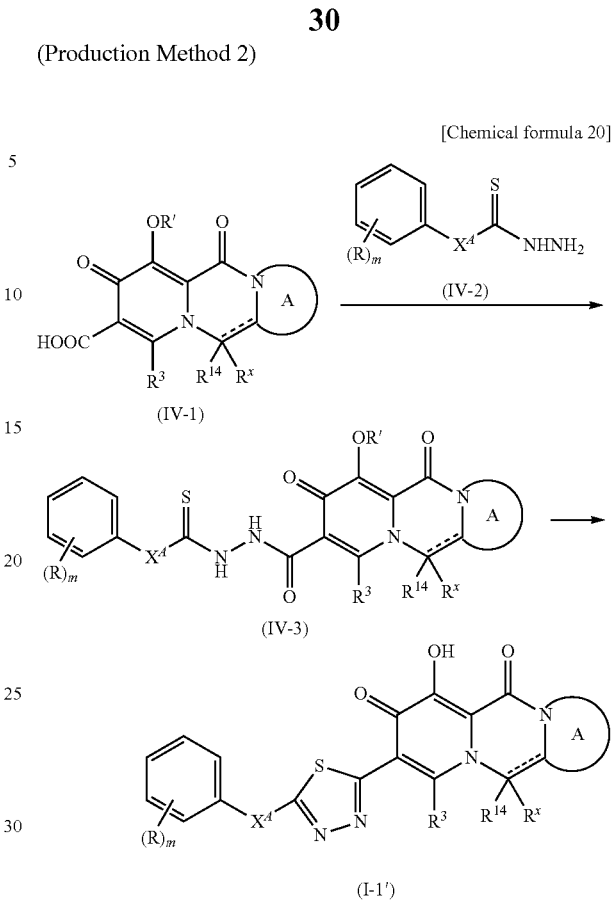

wherein Hal is halogen, R' is a hydroxy-protecting group, and other symbols are defined the same as above.

Q is preferably a 5-membered heterocyclic group that is optionally substituted.

(Step 1)

Compound (II-1) and Compound (II-2) are subjected to a coupling reaction in the presence of a palladium catalyst to obtain Compound (II-3).

Compound (II-1) can be synthesized with a method described in WO2006/116764, WO2010/068262, or the like.

Compound (II-2) is a known compound described in WO2011/105590 or the like, or can be synthesized with a well-known method to those skilled in the art.

A reaction temperature is preferably from room temperature to under heat condition, and more preferably from 40° C. to 150° C., and the present reaction is conducted preferably under nitrogen flow.

A reaction time is preferably from several minutes to several tens of hours, more preferably from several tens of minutes to several hours, and further preferably from 30 minutes to 2 hours.

Examples of reaction solvents include, preferably, DMF, DMA, acetonitrile, toluene, 1,4-dioxane, water, or mixed solvents thereof.

Examples of palladium catalysts include tris(dibenzylideneacetone)dipalladium(0), tetrakis(triphenylphosphine)palladium(0), bis(triphenylphosphine)palladium(II) dichloride, dichloro[1,1'-bis(diphenylphosphino)ferrocene]palladium.

In order to allowing the reaction to proceed suitably, a ligand (e.g., tri(2-furyl)phosphine, tributylphosphine) may be added.

(Step 2)

Compound (II-3) is subjected to a hydroxy-deprotecting reaction, preferably, in the presence of acid to obtain Compound (I-1).

A reaction temperature is preferably from a low temperature to room temperature.

A reaction time is preferably from several minutes to several hours, and preferably from 30 minutes to 2 hours.

Examples of acids include acetic acid, trifluoroacetic acid, phosphoric acid, hydrochloric acid, sulfuric acid, hydrobromic acid.

Examples of solvents include chloroform, hexane, methylene chloride, toluene, alcohol (e.g., methanol, ethanol), ethyl acetate, acetonitrile, dioxane, water, or mixed solvents thereof. In addition, the above-described acids may be used as solvent.

$X^A$ is preferably lower alkylene (e.g., methylene). R is preferably halogen.

(Step 1)

Compound (IV-1) and Compound (IV-2) are reacted, in the presence of base if desired, to obtain Compound (IV-3).

Compound (IV-1) is preferably treated with ethyl chloroformate or the like by a well-known method to those skilled in the art to produce an acid chloride, and then is reacted with Compound (IV-2).

A reaction temperature is preferably from a low temperature to room temperature, and more preferably from under ice-cooling to room temperature.

A room temperature is preferably from several minutes to several tens of hours, more preferably from 10 minutes to several hours, and further preferably from 30 minutes to 2 hours.

Examples of solvents include DMF, chloroform, hexane, methylene chloride, toluene, ethyl acetate, 1,4-dioxane, or mixed solvents thereof.

Examples of bases include preferably organic amines, and more preferably dimethylaminopyridine, and the like.

(Step 2)

Compound (IV-3) is preferably treated with acid to obtain Compound (I-1').

A reaction temperature is preferably from a low temperature to room temperature.

A reaction time is preferably from several minutes to several hours, and preferably from 30 minutes to 2 hours.

Examples of acids include acetic acid, trifluoroacetic acid, phosphoric acid, hydrochloric acid, sulfuric acid, hydrobromic acid.

Examples of solvents include chloroform, hexane, methylene chloride, toluene, alcohol (e.g., methanol, ethanol), ethyl acetate, acetonitrile, dioxane, water, or mixed solvents thereof. In addition, the above-described acids may be used as solvent.

(Production Method 3)

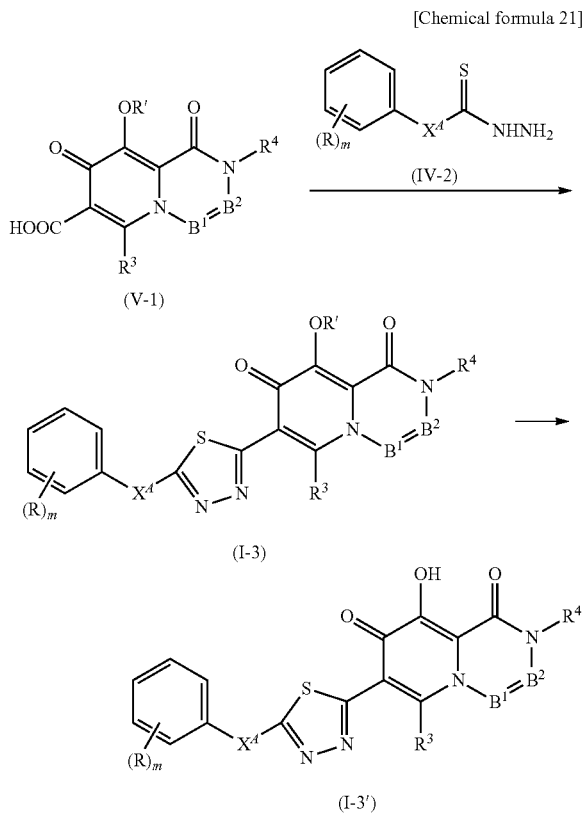

[Chemical formula 21]

wherein each symbol is defined the same as above.

$X^A$ is preferably lower alkylene (e.g., methylene). R is preferably halogen.

(Step 1)

Compound (V-1) and Compound (IV-2) are reacted to obtain Compound (V-3).

Compound (V-1) is preferably converted to an acid chloride by a well-known method to those skilled in the art, and then is reacted with Compound (IV-2).

A reaction temperature is preferably from a low temperature to room temperature.

A reaction time is preferably from several minutes to several tens of hours, more preferably from several tens of minutes to several hours, and further preferably from 30 minutes to 2 hours.

Examples of solvents include chloroform, hexane, methylene chloride, toluene, ethyl acetate, 1,4-dioxane, or mixed solvents thereof.

(Step 2)

Compound (V-3) is subjected to a hydroxy-deprotecting reaction in a similar manner to Production method 1 to obtain Compound (I-3').

The present compound obtained above may be further chemically modified to synthesize another compound. In addition, in the above reaction, when a reactive functional group (e.g., OH, COOH, $NH_2$) is present on a side chain part, etc., the group may be protected before the reaction and may be deprotected after the reaction if desired.

Examples of protecting groups (such as amino protecting group, hydroxy protecting group, and the like) can include protecting groups, such as ethoxycarbonyl, t-butoxycarbonyl, acetyl, benzyl, and the like, which are described in Protective Groups in Organic Synthesis, written by T. W. Greene, John Wiley & Sons Inc. (1991), or the like. Methods for the introduction and removal of a protecting group are methods commonly used in synthetic organic chemistry (see, for example, methods described in Protective Groups in Organic Synthesis, written by T. W. Greene, John Wiley & Sons Inc., (1991) or the like) or can be obtained in accordance therewith. In addition, a functional group included in each substituent can be converted by a known method (for example, those described in Comprehensive Organic Transformations, written by R. C. Larock (1989), and the like) in addition to the above production methods. Some of the compounds of the present invention can be used as a synthetic intermediate, further leading to a new derivative. Intermediates and target compounds produced in each of the above production methods can be isolated and purified by a purification method commonly used in synthetic organic chemistry, for example, subjecting them to neutralization, filtration, extraction, washing, drying, concentration, recrystallization, any kind of chromatography, or the like. In addition, intermediates can be subjected to a next reaction without further purification.

The present compound is useful, for example, as a medicament such as anti-viral agent and the like. The present compound has remarkable inhibitory activity against virus integrase. Therefore, the present compound can be expected to have a preventive or therapeutic effect on various diseases caused by a virus which produces at least integrase and increases at infection in an animal cell; and, for example, it is useful as an integrase inhibiting agent against retroviruses (e.g., HIV-1, HIV-2, HTLV-1, SIV, FIV, etc.); and useful as an anti-HIV agent and the like. A preferred compound also has the following characteristics as pharmacokinetics in the body: the blood concentration is high; the duration of an effect is long; the transitivity to tissue is remarkable; and/or the like. In addition, a preferred compound is safe with regard to a side effect.

In addition, the present compound may be used in a combination therapy in combination with an anti-HIV agent having the different action mechanism such as a reverse transcriptase inhibitor and/or a protease inhibiting agent, etc.

Further, the above use includes not only use as a mixture for anti-HIV, but also use as a concomitant agent for increasing the anti-HIV activity of another anti-HIV agent such as cocktail therapy and the like.

In addition, the present compound can be used to prevent infection with a retrovirus vector from spreading into a tissue other than a target tissue, upon use of a retrovirus vector based on HIV or MLV in the field of gene therapy. Particularly, when a cell or the like is infected with a vector in vitro and then returned into a body, if the present compound is administered in advance, unnecessary infection in the body can be prevented.

The present compound can be administered orally or parenterally. In the case of oral administration, the present compound can be also used as a conventional preparation, for example, as any dosage form of a solid agent such as tablet, powder, granule, capsule, and the like; pharmaceutical solution; oleaginous suspension; liquid such as syrup and elixir; or the like. In the case of parenteral administration, the present compound can be used as an aqueous or oleaginous suspended injection, or a nasal drop. Upon preparation of it, any conventional excipients, binders, lubricants, aqueous solvents, oleaginous solvents, emulsifiers, suspending agents, preservatives, stabilizers and the like may be used. In addition, as an anti-HIV agent, an oral agent is particularly preferred. A preparation of the present invention is produced by combining (e.g. mixing) a therapeutically effective amount of the present compound with a pharmaceutically acceptable carrier or diluent.

The dose of a compound of the present invention varies depending on an administration method, the age, weight and condition of a patient and the type of a disease. Usually, in the case of oral administration, about 0.05 mg to 3000 mg, preferably about 0.1 mg to 1000 mg, may be administered per adult daily, if necessary, by dividing the dose. In addition, in the case of parenteral administration, about 0.01 mg to 1000 mg, preferably about 0.05 mg to 500 mg, is administered per adult daily.

EXAMPLES

Hereinafter, Examples are described.

ABBREVIATION

DMF: dimethylformamide
Bn: benzyl
$PdCl_2$(dppf): dichloro[1,1'-bis(diphenylphosphino)ferrocene]palladium

Example 1

[Chemical formula 22]

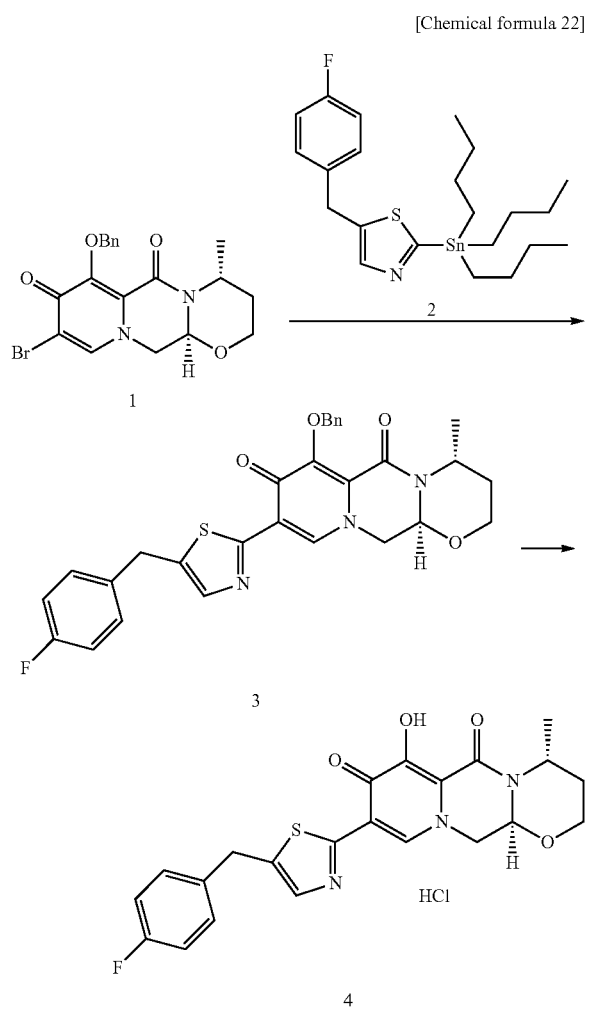

3.57 mmol) and $PdCl_2$(dppf) (175 mg, 0.239 mmol), and then the reaction mixture was stirred at 110° C. for 1 hour. After the resulting reaction solution was stood to cool to room temperature, it was diluted with ethyl acetate (50 ml), and then aqueous saturated potassium fluoride solution (50 ml) was added thereto, followed by stirring overnight. After the precipitated insolubles were filtered, separation was performed, and then the aqueous layer was extracted with ethyl acetate twice. After the combined organic layer was washed with water three times and dried over sodium sulfate, the solvent was evaporated off. The resulting crude product was purified by subjecting it to silica gel column chromatography. Firstly, it was eluted with hexane-ethyl acetate (1:1, v/v), then eluted with ethyl acetate only. The target fractions were concentrated to yield Compound 3 (1.04 g, 82% yield).

$^1$H-NMR (CDCl$_3$) δ: 1.32 (d, J=7.2 Hz, 3H), 1.49 (dd, J=2.1 Hz, 13.5 Hz, 1H), 2.09-2.21 (m, 1H), 3.91-3.95 (m, 2H), 4.10 (dd, J=6.0 Hz, 13.2 Hz, 1H), 4.15 (s, 2H), 4.24 (dd, J=3.9 Hz, 13.2 Hz, 1H), 4.95-5.04 (m, 1H), 5.15-5.19 (m, 1H), 5.34 (d, J=13.2 Hz, 1H), 5.42 (d, J=13.2 Hz, 1H), 6.95-7.02 (m, 2H), 7.19-7.36 (m, 5H), 7.54 (s, 1H), 7.66 (d, J=6.9 Hz, 2H), 8.40 (s, 1H).

Step 2 Synthesis of Compound 4

Compound 3 (1.00 g, 1.88 mmol), obtained from Step 1, was dissolved in trifluoroacetic acid (10.0 ml), and then the reaction mixture was stirred at room temperature for 1 hour. The reaction solution was concentrated, and then chloroform was added thereto. After concentration of this, 4 N hydrochloric acid/ethyl acetate solution was added thereto, and then this was concentrated. The resulting solid was suspended in ethyl acetate, and then filtered to yield Compound 4 (888 mg, 99% yield).

$^1$H-NMR (DMSO-d$_6$) δ: 1.34 (d, J=6.9 Hz, 3H), 1.55 (d, J=12.6 Hz, 1H), 1.99-2.07 (m, 1H), 3.88-3.93 (m, 1H), 3.99-4.08 (m, 1H), 4.20 (s, 2H), 4.39 (dd, J=5.7 Hz, 13.8 Hz), 4.60 (dd, J=3.9 Hz, 13.8 Hz), 4.78-4.83 (m, 1H), 5.46-5.49 (m, 1H), 7.17 (t, J=8.7 Hz, 2H), 7.32-7.37 (m, 2H), 7.69 (s, 1H), 8.78 (s, 1H).

Example 2

The following compound was synthesized by a similar procedure to Example 1.

[Chemical formula 23]

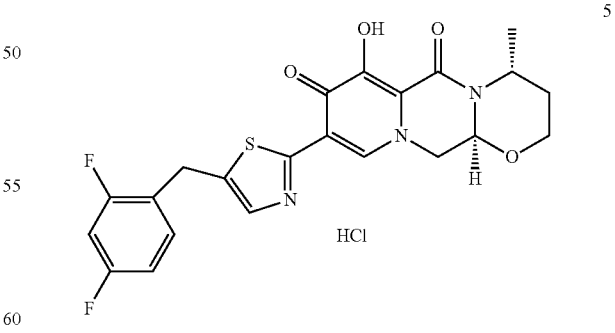

$^1$H-NMR (DMSO-d$_6$) δ: 1.35 (d, J=7.2 Hz, 3H), 1.55 (d, J=12.6 Hz, 1H), 1.96-2.07 (m, 1H), 3.88-3.93 (m, 1H), 4.02-4.08 (m, 1H), 4.22 (s, 2H), 4.39 (dd, J=5.7 Hz, 13.8 Hz, 1H), 4.60 (dd, J=3.9 Hz, 13.8 Hz), 4.79-4.85 (m, 1H), 5.46-5.49 (m, 1H), 7.04-7.11 (m, 1H), 7.21-7.28 (m, 1H), 7.46 (dd, J=8.7 Hz, 15.6 Hz, 1H), 7.66 (s, 1H), 8.74 (s, 1H).

Step 1 Synthesis of Compound 3

Under nitrogen flow, to a solution of Compound 1 (1.00 g, 2.39 mmol) in DMF (5 ml) was added Compound 2 (1.72 g,

Example 3

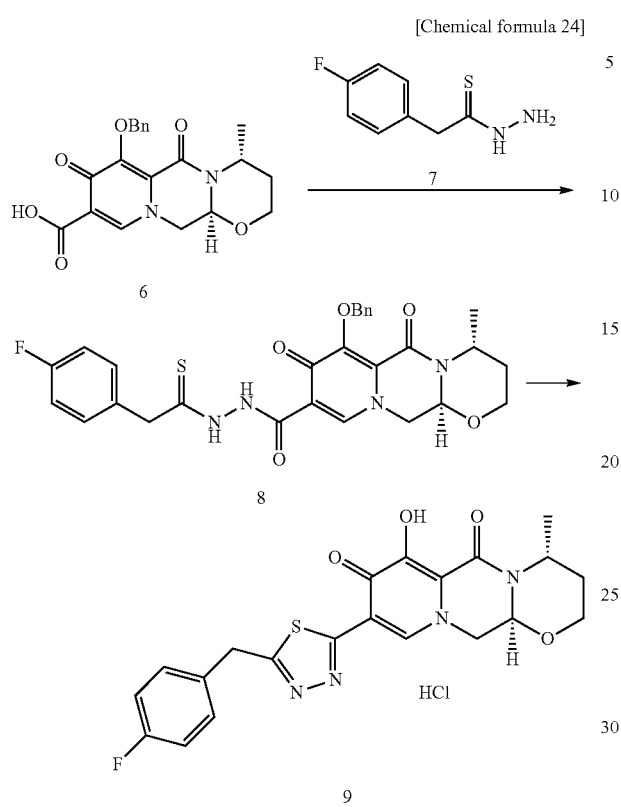

Example 4

The following compound was synthesized by a similar procedure to Example 3.

[Chemical formula 25]

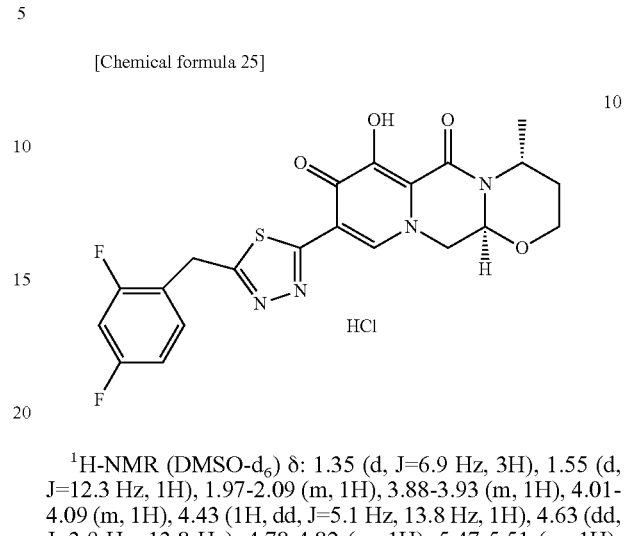

$^1$H-NMR (DMSO-d$_6$) δ: 1.35 (d, J=6.9 Hz, 3H), 1.55 (d, J=12.3 Hz, 1H), 1.97-2.09 (m, 1H), 3.88-3.93 (m, 1H), 4.01-4.09 (m, 1H), 4.43 (1H, dd, J=5.1 Hz, 13.8 Hz, 1H), 4.63 (dd, J=3.9 Hz, 13.8 Hz), 4.78-4.82 (m, 1H), 5.47-5.51 (m, 1H), 7.08-7.14 (m, 1H), 7.25-7.32 (m, 1H), 7.50-7.58 (m, 1H), 8.90 (s, 1H).

Example A

The following compounds are synthesized.

[Chemical formula 26]

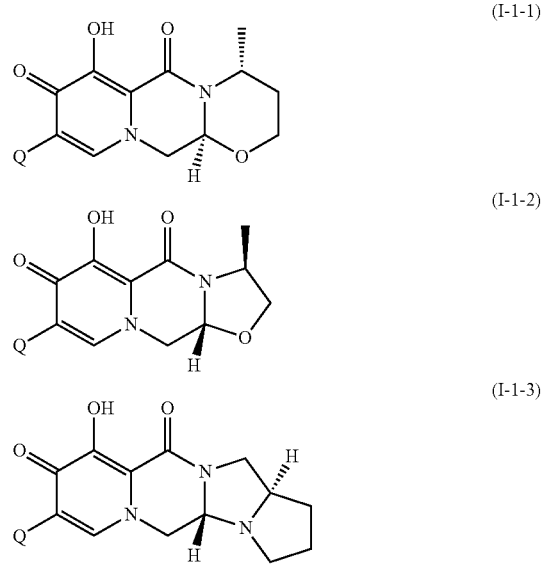

Q is any substituent of the following.

[Chemical formula 27]

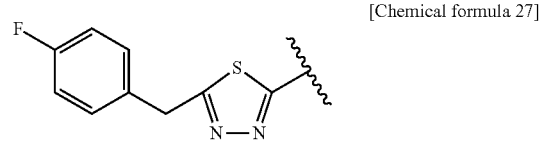

Step 1 Synthesis of Compound 8

To a solution of Compound 6 (200 mg, 0.52 mmol) in DMF (5 ml), under ice-cooling, was added triethylamine (263 mg, 2.60 mmol) and ethyl chloroformate (169 mg, 1.56 mmol). After stirring at the same temperature for 10 minutes, Compound 7 (287 mg, 1.56 mmol) and dimethylaminopyridine (6 mg, 0.05 mmol) were added thereto, and then the reaction mixture was stirred at the same temperature for 1 hour. After water was added to the resulting reaction solution and it was washed with ethyl acetate three times, the aqueous layer was extracted with chloroform twice. After the combined extract liquid was dried over sodium sulfate, the solvent was evaporated off. The resulting crude product was purified by subjecting it to silica gel column chromatography. Firstly, it was eluted with chloroform only, and then eluted with chloroform-methanol (3:2, v/v). The target fractions were concentrated to yield Compound 8 (109 mg, 38% yield). $^1$H-NMR (CDCl$_3$) δ: 1.31 (d, J=6.9 Hz, 3H), 1.49 (d, J=12.3 Hz, 1H), 2.04-2.19 (m, 1H), 3.93 (d, J=8.7 Hz, 2H), 3.40-4.06 (m, 1H), 4.08-4.20 (m, 1H), 4.13 (s, 2H), 4.94-4.99 (m, 1H), 5.13-5.16 (m, 1H), 5.37 (d, J=9.9 Hz, 1H), 5.44 (d, J=9.9 Hz, 2H), 7.06 (t, J=8.4 Hz, 2H), 7.19-7.35 (m, 5H), 7.58-7.60 (m, 2H), 8.12 (s, 1H), 10.43 (br, 1H), 13.71 (s, 1H).

Step 2 Synthesis of Compound 9

Compound 8 (109 mg, 0.92 mmol), obtained from Step 1, was dissolved in 4 N hydrochloric acid/dioxane solution (3.0 ml), and then the reaction mixture was stirred at room temperature for 30 minutes. After the precipitated solid was filtered, it was suspended in di-isopropyl ether, and then filtered to yield Compound 9 (62 mg, 65% yield).

$^1$H-NMR (DMSO-d$_6$) δ: 1.35 (d, J=6.9 Hz, 3H), 1.55 (d, J=9.6 Hz, 1H), 1.97-2.07 (m, 1H), 3.91 (dd, J=3.6 Hz, 11.4 Hz, 1H), 4.05 (t, J=10.2 Hz, 1H), 4.39-4.49 (m, 1H), 4.47 (s, 1H), 4.60-4.66 (m, 1H), 4.80 (t, J=6.3 Hz, 1H), 5.47-5.50 (m, 1H), 7.18 (t, J=9.0 Hz, 2H), 7.39-7.44 (m, 2H), 8.90 (s, 1H).

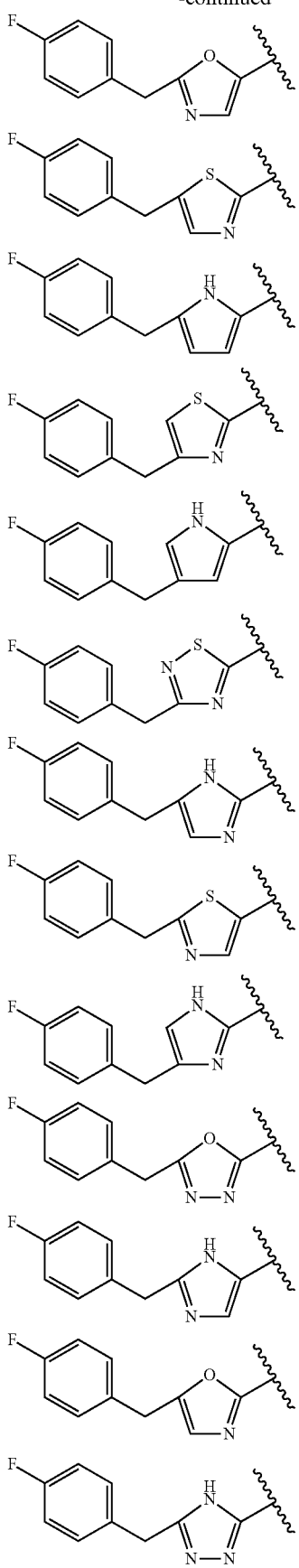
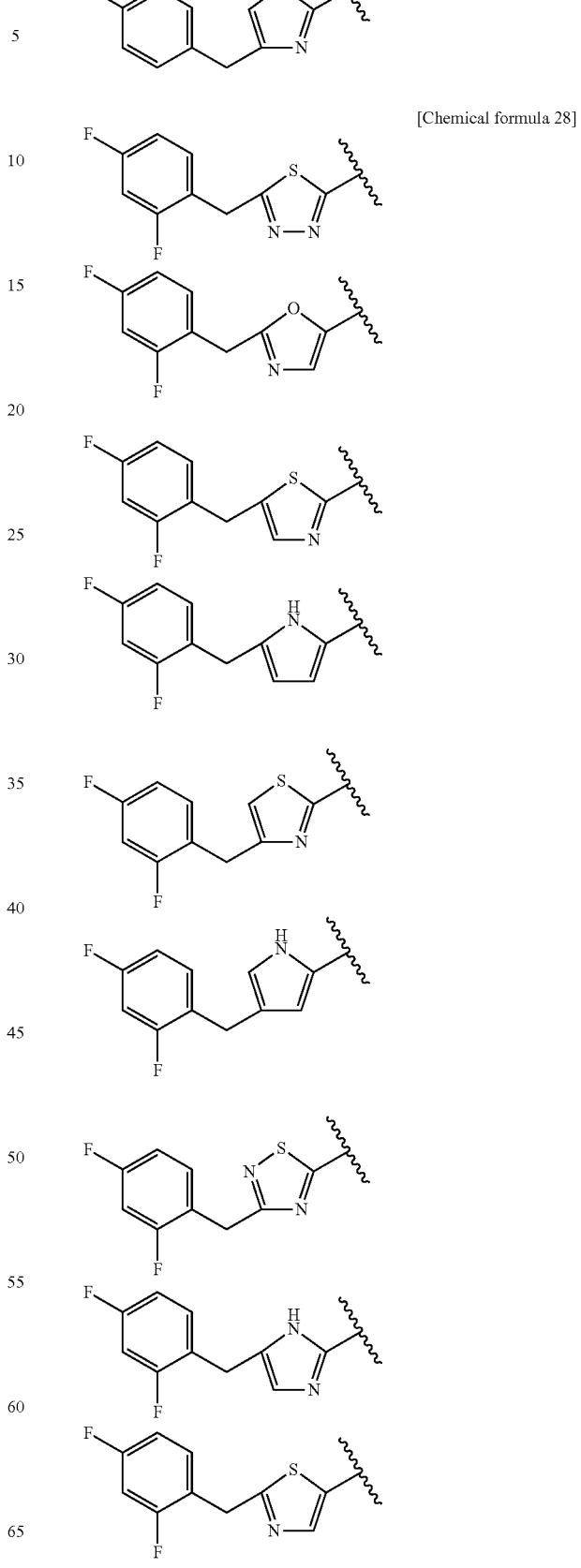

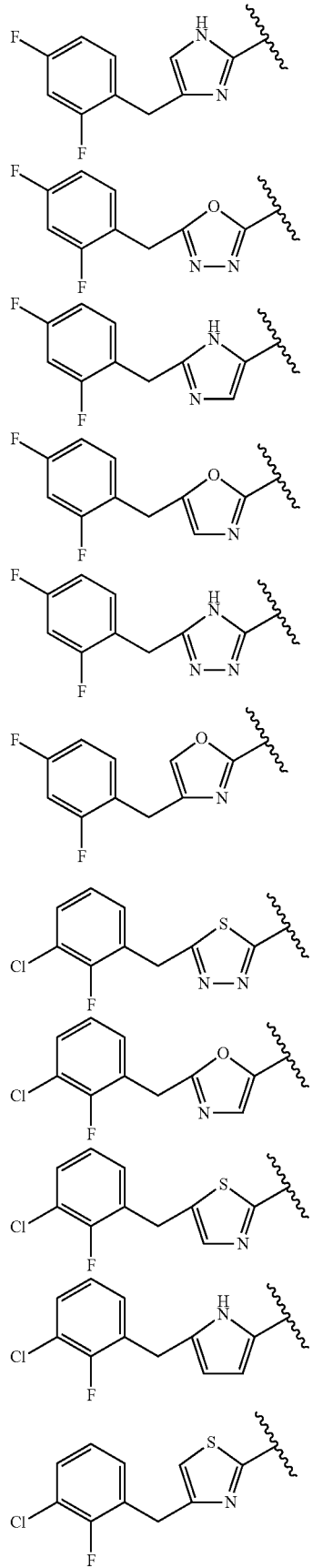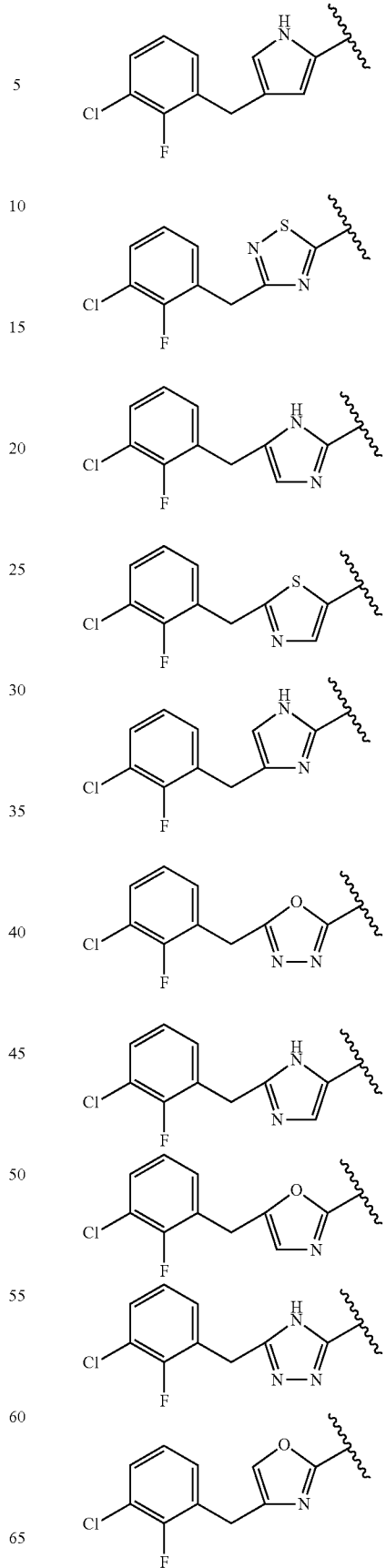

Experimental Example 1

Integrase Inhibitory Activity (Test Method)

(1) Preparation of DNA Solution

By the same method as that described in Experimental Example 1 of Patent Document 2, a substrate DNA solution (2 pmol/µl) and a target DNA solution (5 pmol/µl) were prepared. After each target DNA solution was once boiled, a temperature was slowly lowered to anneal complementary strands, which was then used. Each sequence of a substrate DNA and a target DNA is as described in the same Experimental Example.

(2) Measurement of Inhibition Rate ($IC_{50}$ Value)

Onto Immobilizer—Streptavidin Plates (manufactured by NUNC) was added 100 µl of a substrate DNA solution (2 pmol/µl). After adsorbing at room temperature for 60 minutes under shaking, it was washed with a phosphate buffer two times.

Then, to each well prepared as described above were added 51 µl of a reaction solution prepared from 12 µl of a buffer (composition: 150 mM MOPS (pH 7.2), 75 mM $MnCl_2$, 50 mM 2-mercaptoethanol, 25% glycerol, 500 µg/ml bovine serum albumin-fraction V) and 39 µl of distilled water. Then, 9 µl of an integrase solution (30 pmol) was added, and the mixture was mixed well. To a well as a negative control (NC) was added 9 µl of a diluting solution (composition: 50 mM Hepes (pH 8.0), 10 mM DTT, 10% Glycerol, 0.5 M NaCl), and this was mixed well using a plate mixer.

After the plate was incubated at 30° C. for 60 minutes, the reaction solution was discarded, followed by washing with 200 µl of a washing buffer (composition: 150 mM MOPS (pH 7.2), 50 mM 2-mercaptoethanol, 25% glycerol, 500 µg/ml bovine serum albumin-fraction V) three times.

Then, to each well were added 53 µl of a reaction solution prepared from 12 µl of a buffer (composition: 150 mM MOPS (pH 7.2), 75 mM $MgCl_2$, 50 mM 2-mercaptoethanol, 25% glycerol, 500 µg/ml bovine serum albumin-fraction V) and 41 µl of distilled water. Further, 6 µl of a solution of a test compound in DMSO was added to each well, and 6 µl of DMSO was added to wells as a positive control (PC) and a negative control (NC), followed by mixing well using a plate mixer. After the plate was incubated at 30° C. for 60 minutes, 1 µl of a target DNA (5 pmol/µl) was added, and this was mixed well using a plate mixer.

After each plate was incubated at 30° C. for 10 minutes, the reaction solution was discarded, followed by washing with a phosphate buffer two times. Then, an anti-digoxigenin antibody labeled with alkaline phosphatase (sheep Fab fragment: manufactured by Boehringer) was diluted 2000-fold with an antibody diluting solution, 100 µl of the diluent was added to bind at 30° C. for 1 hour, and this was washed successively with a phosphate buffer containing 0.05% Tween 20 two times, and a phosphate buffer two times. Then, 150 µl of an alkaline phosphatase coloring buffer (composition: 0.9 mM para-nitrophenyl phosphate (manufactured by PIERCE), 1 M diethanolamine (Thermo; pH 9.8)) was added to react at 30° C. for 1 hour, an absorbance (OD 405 nm) of each well was measured, and an inhibition rate ($IC_{50}$) was obtained according to the following calculation formula.

Inhibition rate (%)=100[1−{(C abs.−NC abs.)/(PC abs.−NC abs.)}]

C abs.: Absorbance of well of compound
NC abs.: Absorbance of NC
PC abs.: Absorbance of PC

TABLE 1

| Example | Compound No. | IC50 (nM) |
|---------|--------------|-----------|
| 1 | 4 | 3.9 |
| 2 | 5 | 2.0 |
| 3 | 9 | 3.8 |
| 4 | 10 | 1.3 |

Experimental Example 2

Anti-HIV Activity (Test Method)

Previously, a series of two-fold dilution on test samples were carried out in a 96-well plate (50 µL/well). Two plates were made for measuring anti-HIV activity and measuring cytotoxicity. For each agent, measurement in duplicate was carried out. An MT-4 cell suspension of $2.5 \times 10^5$/mL was dispensed at 100 µL/well onto the 96-well plate containing the test samples. An HIV virus solution was dispensed at 50 µL/well onto the 96-well plate containing the test samples and the cell. To the plate for measuring cytotoxicity, a culture solution was dispensed at 50 µL/well. It was mixed by a plate mixer, and then incubated in a $CO_2$ incubator for 4 days. The 96-well plate incubated for 4 days was observed with the naked eye and under a microscope, and it was confirmed that there is no problem with virus proliferation and inhibition in the wells of the positive control and the negative control. Thirty microliters of a MTT (3-(4,5-dimethylthiazol-2-yl)-2,5-diphenyltetrazolium bromide) solution was dispensed to each well.

A reaction was allowed to occur in a $CO_2$ incubator for 1 hour. From each well, 150 µL of the supernatant was removed such that cells are not sucked. One-hundred and fifty microliters of a cell lysis solution was added thereto, and then it was mixed well by a plate mixer until the whole cells are lysed. The mixed 96-well plates were measured by a microplate reader at two wavelengths, 560 nm/690 nm. Based on the following calculation formula, 50% HIV inhibition concentration (EC50) was calculated.

$$EC50 = 10^Z$$

$$Z = (50\% - \text{Low \%})/(\text{High \%} - \text{Low \%}) \times \{\log(\text{High conc.}) - \log(\text{Low conc.})\} + \log(\text{Low conc.})$$

Based on the following calculation formula, 50% cytotoxic concentration (CC50) was calculated.

$$CC50 = 10^Z$$

$$Z = (50\% - \text{Low \%})/(\text{High \%} - \text{Low \%}) \times \{\log(\text{High conc.}) - \log(\text{Low conc.})\} + \log(\text{Low conc.})$$

Based on the following calculation formula, selectivity index was calculated.

$$SI = CC50/EC50$$

(Result)

TABLE 2

| Example | Compound No. | EC50 (nM) |
|---------|--------------|-----------|
| 2 | 5 | 2.8 |
| 4 | 10 | 1.7 |

Formulation Example

A term "active ingredient" means the present compound, a tautomer thereof, a pharmaceutically acceptable salt thereof, or a solvate thereof.

Formulation Example 1

A hard gelatin capsule is prepared using the following ingredients:

|   | Dose (mg/capsule) |
|---|---|
| Active ingredient | 250 |
| Starch (dried) | 200 |
| Magnesium stearate | 10 |
| Total | 460 mg |

Formulation Example 2

A tablet is prepared using the following ingredients:

|   | Dose (mg/capsule) |
|---|---|
| Active ingredient | 250 |
| Cellulose (microcrystalline) | 200 |
| Silicon dioxide (fumed) | 10 |
| Stearic acid | 5 |
| Total | 665 mg |

Ingredients are mixed, and compressed to obtain tablets, each weighing 665 mg.

INDUSTRIAL APPLICABILITY

The present compound has integrase inhibitory activity and/or cell proliferation inhibitory activity against viruses, in particular, HIV. Thus, the compound is useful in preventing or treating various diseases, viral infections (e.g., AIDS), and the like in which integrase participates.

The invention claimed is:
1. A compound represented by the formula (I-1):

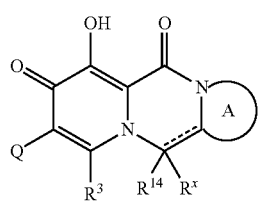

(I-1)

wherein:
Q is:
cycloalkyl that is optionally substituted and optionally condensed,
cycloalkenyl,
aryl that is optionally substituted and optionally condensed, or
a heterocyclic group selected from a 5-7 membered saturated or unsaturated non-aromatic ring having at least one of nitrogen, oxygen, phosphorus and sulfur atoms in the ring and a 5-8 membered aromatic ring having one to four of oxygen, sulfur, phosphorus and nitrogen atoms in the ring, wherein said heterocyclic group is optionally substituted and optionally condensed;
$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, an optionally substituted heterocyclic group, an optionally substituted heterocyclyloxy group, or optionally substituted amino;
the A ring is an optionally substituted heterocycle selected from any of (a)-(i):

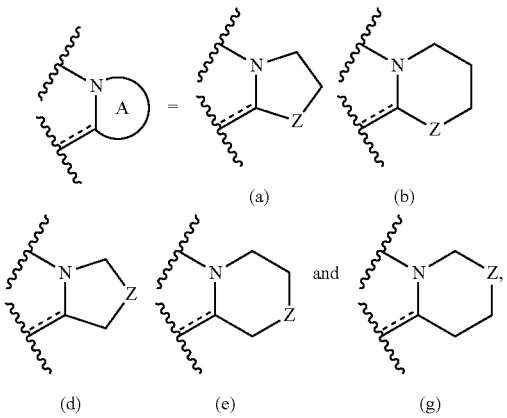

wherein Z is O;
$R^{14}$ and $R^X$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, an optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of O, S, SO, $SO_2$, $NR^5$ (wherein $R^5$ is, independent of $R^4$, selected from the same substituent group as $R^4$), —N=, and =N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, or optionally substituted aminocarbonyl;

the broken line represents the presence or absence of a bond;

with the proviso that when the broken line represents the presence of a bond, $R^X$ is not present;

when a substituent is present on said "optionally substituted lower alkyl", "optionally substituted cycloalkyl", "optionally substituted cycloalkyl lower alkyl", "optionally substituted lower alkenyl", "optionally substituted lower alkoxy", "optionally substituted aryl", "optionally substituted aryl lower alkyl", "optionally substituted aryloxy", "optionally substituted heterocycle", "optionally substituted heterocyclic group", "optionally substituted heterocyclyl lower alkyl", "optionally substituted heterocyclyloxy", "optionally substituted lower alkenyloxy", "optionally substituted lower alkylcarbonyl", "optionally substituted cycloalkylcarbonyl", "optionally substituted cycloalkyl lower alkylcarbonyl", "optionally substituted lower alkoxycarbonyl", "optionally substituted arylcarbonyl", "optionally substituted aryl lower alkylcarbonyl", "optionally substituted aryloxycarbonyl", "optionally substituted heterocyclylcarbonyl", "optionally substituted heterocyclyl lower alkylcarbonyl", "optionally substituted heterocyclyloxycarbonyl", "optionally substituted lower alkylene", "optionally substituted lower alkenylene", or "optionally substituted phosphoric acid residue", each substituent may be the same or different, 1 to 4 group(s) selected from Substituent group B and Substituent group A at any position;

Substituent group B consists of hydroxy, carboxy, halogen, halo lower alkyl, halo lower alkoxy, lower alkyl, lower alkenyl, lower alkynyl, cycloalkyl, cycloalkenyl, lower alkoxy, lower alkenyloxy, lower alkoxycarbonyl, nitro, nitroso, optionally substituted amino, azido, aryl, aralkyl, cyano, isocyano, isocyanato, thiocyanato, isothiocyanato, mercapto, alkylthio, alkylsulfonyl, methanesulfonylamino, ethanesulfonylamino, N-methylsulfonyl-N'-methylamino, optionally substituted carbamoyl, sulfamoyl, acyl, formyloxy, haloformyl, oxalo, thioformyl, thiocarboxy, dithiocarboxy, thiocarbamoyl, sulfino, sulfo, sulfoamino, hydrazino, azido, ureido, amidino, guanidino, phthalimido, oxo, phosphoric acid residue, phosphoric-acid-residue-substituted lower alkyl (which may be intervened by a heteroatom group), aryl substituted with a phosphoric acid residue, aralkyl substituted with a phosphoric acid residue, and hydroxy lower alkyl;

Substituent group A consists of alkyl, lower alkoxy, halogen, halogenated lower alkyl, halogenated lower alkoxy, and the formula:

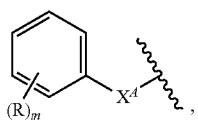

(B)

wherein $X^A$ is a group selected from the following group:
$X^{41}$: a single bond;
$X^{42}$: a group selected from C=O and C=S;
$X^{43}$: a heteroatom group selected from O, S, SO, SO$_2$, and NR$^{1'}$ wherein R$^{1'}$ is hydrogen or lower alkyl;
$X^{44}$: a group formed by linking the same or different, two or more groups selected from $X^{42}$ and $X^{43}$;
$X^{45}$: a group selected from —N=N—, —C(R$^{1'}$)=N—, or —N=C(R$^{1'}$)— wherein R$^{1'}$ is hydrogen or lower alkyl;
$X^{46}$: optionally substituted lower alkylene or optionally substituted lower alkenylene;
$X^{47}$: $X^{46}$ intervened by one or any two or more groups selected from $X^{42}$, $X^{43}$, $X^{44}$, and $X^{45}$; and
$X^{48}$: a spacer consisting of any combination of $X^{41}$ to $X^{47}$;

R is a group independently selected from the following group:
(1) lower alkyl,
(2) lower alkoxy,
(3) halogen,
(4) halogenated lower alkyl,
(5) halogenated lower alkoxy, and
(6) lower cycloalkyl; and m is an integer of 0 to 5;

the substituent of said "optionally substituted amino" or "optionally substituted carbamoyl" is independently selected from mono- or di-lower alkyl, lower alkylcarbonyl, or lower alkylsulfonyl, optionally substituted lower alkyl, lower alkoxy lower alkyl, formyl, optionally substituted lower alkylcarbonyl, lower alkoxy lower alkylcarbonyl, lower alkylcarbamoyl lower alkylcarbonyl, alkoxycarbonylacetyl, optionally substituted arylcarbonyl, optionally substituted aralkyl, hydroxy, methanesulfonyl, ethanesulfonyl, isopropylsulfonyl, 2,2,2-trifluoroethanesulfonyl, benzylsulfonyl, methoxyethylsulfonyl, arylsulfonyl optionally substituted with lower alkyl or halogen, cycloalkyl, aryl optionally substituted with lower alkyl, lower alkylaminosulfonyl, lower alkylaminocarbonyl, lower alkoxycarbonyl, cycloalkylcarbonyl, sulfamoyl, methylsulfamoyl, dimethylsulfamoyl, lower alkylcarbonylamino, heterocycle, and optionally substituted amino, wherein any two substituents on the amino group of "optionally substituted amino", "optionally substituted aminocarbonyl", or "optionally substituted carbamoyl" may together with the adjacent nitrogen atom may form a nitrogen-containing heterocycle which may contain at least one of sulfur and oxygen atoms in the ring, wherein the ring is optionally substituted with oxo or hydroxy, and the sulfur atom forming the ring may be substituted with oxo;

or a pharmaceutically acceptable salt thereof.

2. The compound according to claim 1, or a pharmaceutically acceptable salt thereof, wherein Q is an optionally substituted heterocyclic group selected from a 5-7 membered saturated or unsaturated non-aromatic ring having at least one of nitrogen, oxygen, phosphorus and sulfur atoms in the ring and a 5-8 membered aromatic ring having one to four of oxygen, sulfur, phosphorus and nitrogen atoms in the ring, wherein said heterocyclic group is optionally substituted and optionally condensed.

3. The compound according to claim 2, or a pharmaceutically acceptable salt thereof, wherein the "heterocyclic group" of Q is a 5-7 membered monocyclic heterocyclic group.

4. The compound according to claim 2, or a pharmaceutically acceptable salt thereof, wherein the heterocyclic group of the "optionally substituted heterocyclic group" of Q is represented by a formula selected from the following:

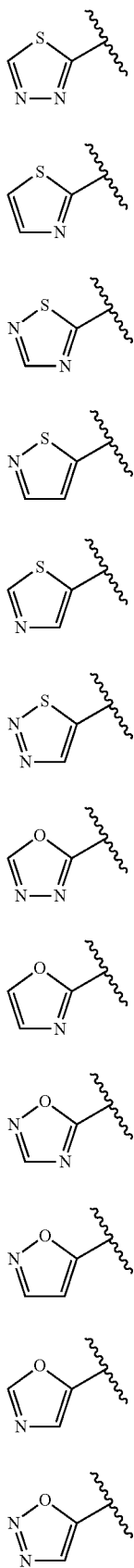

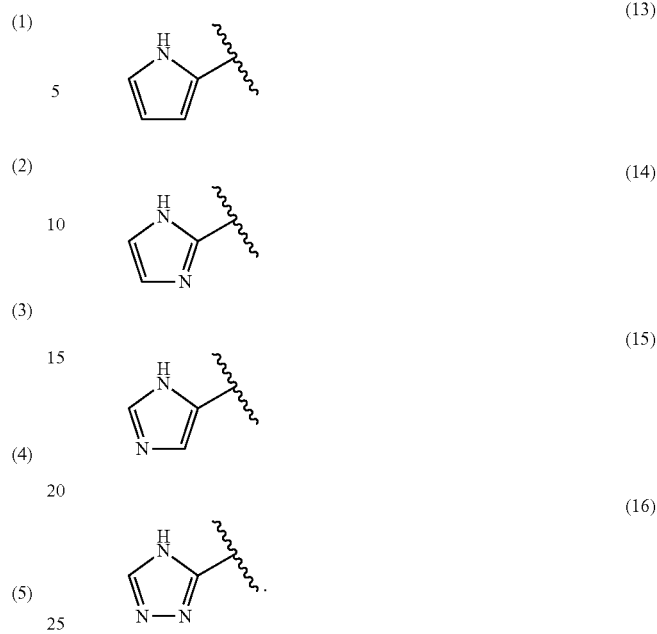

5. The compound according to any of claims 1 and 2-4, or a pharmaceutically acceptable salt thereof, wherein the substituent(s) in the "optionally substituted" Q are the same or different, 1 to 4 substituent(s) selected from Substituent group A—that consists of: lower alkyl, lower alkoxy, halogen, halogenated lower alkyl, halogenated lower alkoxy, and the formula:

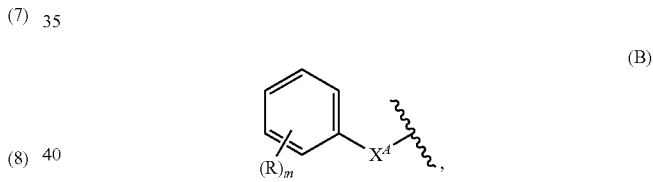

wherein
$X^A$ is a group selected from the following group:
$X^{A1}$: a single bond;
$X^{A2}$: a group selected from C=O and C=S;
$X^{A3}$: a heteroatom group selected from O, S, SO, SO$_2$, and NR$^{1'}$ wherein R$^{1'}$ is hydrogen or lower alkyl;
$X^{A4}$: a group formed by linking the same or different, two or more groups selected from $X^{A2}$ and $X^{A3}$;
$X^{A5}$: a group selected from —N=N—, —C(R$^{1'}$)=N—, or —N=C(R$^{1'}$)— wherein R$^{1'}$ is hydrogen or lower alkyl;
$X^{A6}$: optionally substituted lower alkylene or optionally substituted lower alkenylene;
$X^{A7}$: $X^{A6}$ intervened by one or any two or more groups selected from $X^{A2}$, $X^{A3}$, $X^{A4}$, and $X^{A5}$; and
$X^{A8}$: a spacer consisting of any combination of $X^{A1}$ to $X^{A7}$;
R is a group independently selected from the following group:
(1) lower alkyl,
(2) lower alkoxy,
(3) halogen,
(4) halogenated lower alkyl,
(5) halogenated lower alkoxy, and
(6) lower cycloalkyl; and
m is an integer of 0 to 5.

6. The compound according to claim 1, or a pharmaceutically acceptable salt thereof, wherein Q is represented by a formula selected from the following:

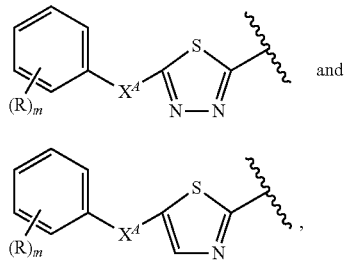

wherein each symbol is defined the same as claim 5.

7. The compound according to claim 6, or a pharmaceutically acceptable salt thereof, wherein $X^A$ is lower alkylene; R is independently lower alkoxy, halogen, or halogenated lower alkyl; and m is 1 or 2.

8. The compound according to claim 1, or a pharmaceutically acceptable salt thereof, wherein the compound is represented by a formula selected from the following:

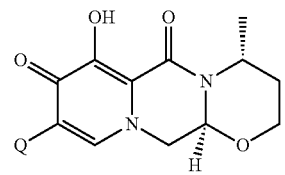

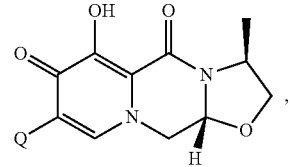

wherein Q is defined the same as claim 1.

9. A pharmaceutical composition comprising a compound according to any of claims 1 and 2-4, or a pharmaceutically acceptable salt thereof.

10. The pharmaceutical composition according to claim 9, which has anti-HIV activity.

11. The pharmaceutical composition according to claim 9, which has an HIV integrase inhibitory activity.

* * * * *